United States Patent
Kim et al.

(10) Patent No.: US 10,017,456 B2
(45) Date of Patent: Jul. 10, 2018

(54) MONOMER AND POLYMER AND COMPENSATION FILM AND OPTICAL FILM AND DISPLAY DEVICE

(71) Applicant: SAMSUNG ELECTRONICS CO., LTD., Suwon-si, Gyeonggi-do (KR)

(72) Inventors: Changki Kim, Suwon-si (KR); Dmitry Androsov, Suwon-si (KR); Masashi Tsuji, Hwaseong-si (KR); Hyunseok Choi, Anyang-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/171,453

(22) Filed: Jun. 2, 2016

(65) Prior Publication Data

US 2017/0197906 A1    Jul. 13, 2017

(30) Foreign Application Priority Data

Jan. 7, 2016 (KR) .................. 10-2016-0002148

(51) Int. Cl.
*C07C 69/82* (2006.01)
*C08G 64/04* (2006.01)
(Continued)

(52) U.S. Cl.
CPC .............. *C07C 69/82* (2013.01); *C07C 69/76* (2013.01); *C08G 64/045* (2013.01); *C08L 69/005* (2013.01); *G02B 5/3083* (2013.01)

(58) Field of Classification Search
CPC ..... C07C 69/82; C08G 64/045; C08L 69/005; G02B 5/3083
(Continued)

(56) References Cited

U.S. PATENT DOCUMENTS 4,657,708 A    4/1987 Evers et al.
4,663,425 A    5/1987 Evers et al.

FOREIGN PATENT DOCUMENTS

WO    WO 2010/072760 A1 *  7/2010 ............. C08G 65/00

OTHER PUBLICATIONS

STIC Search Report dated Oct. 17, 2017.*
(Continued)

*Primary Examiner* — Eisa B Elhilo
(74) *Attorney, Agent, or Firm* — Cantor Colburn LLP

(57) ABSTRACT

A monomer is represented by Chemical Formula 1:

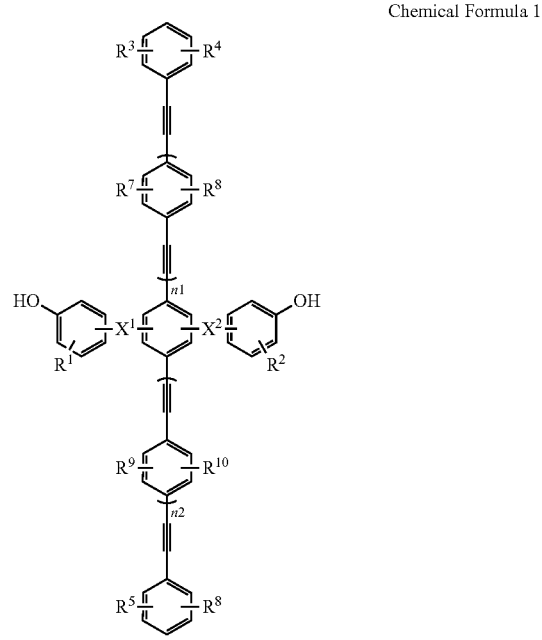

Chemical Formula 1 wherein in Chemical Formula 1, $X^1$ and $X^2$ are independently O, C(=O), or C(=O)O, $R^1$ to $R^{10}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to
(Continued)

C20 heterocyclic group, a substituted or unsubstituted silyl group, a hydroxy group, a halogen, a nitro group, or a combination thereof, and n1 and n2 are independently an integer ranging from 0 to 3.

27 Claims, 5 Drawing Sheets

(51) Int. Cl.
 *C08L 69/00* (2006.01)
 *G02B 5/30* (2006.01)
 *C07C 69/76* (2006.01)
(58) Field of Classification Search
 USPC ............................................. 359/489.02
 See application file for complete search history.

(56) References Cited

OTHER PUBLICATIONS

Robert C. Evers et al. "Aromatic Polyamides Containing Pendant Phenylacetylene Groups", Polymer Preprints (American Chemical Society, Division of Polymer Chemistry) (1985), 26(1), 140-1.
Robert C. Evers et al. "Thermally Reactive Aromatic Polyamides", Journal of Polymer Science: Part A: Polymer Chemistry, vol. 26, 3213-3228 (1988).

* cited by examiner

MONOMER AND POLYMER AND COMPENSATION FILM AND OPTICAL FILM AND DISPLAY DEVICE

CROSS-REFERENCE TO RELATED APPLICATION

This application claims priority to Korean Patent Application No. 10-2016-0002148 filed in the Korean Intellectual Property Office on Jan. 7, 2016, and all the benefits accruing therefrom under 35 U.S.C. § 119, the content of which is incorporated herein in its entirety by reference.

BACKGROUND

1. Field

A monomer, a polymer, a compensation film, an optical film, and a display device are disclosed.

2. Description of the Related Art

A flat panel display may be classified into a light-emitting display device emitting light by itself and a non-emissive display device requiring a separate light source, wherein a compensation film is employed for improving the image quality thereof. There remains a need in novel polymers, which can improve the properties of the existing compensation and optical films.

SUMMARY

An embodiment provides a novel monomer that is applicable in a compensation film.

Another embodiment provides a polymer obtained by polymerization of the novel monomer.

Yet another embodiment provides a compensation film including the polymer.

Still another embodiment provides a display device including the compensation film.

Further another embodiment provides a display device including the compensation film or the optical film.

According to an embodiment, a monomer represented by Chemical Formula 1 is provided.

Chemical Formula 1

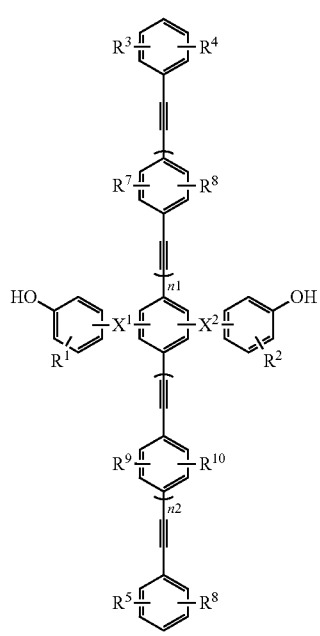

In Chemical Formula 1, $X^1$ and $X^2$ are independently O, C(=O), or C(=O)O, $R^1$ to $R^{10}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and n1 and n2 are independently an integer ranging from 0 to 3.

The monomer may be represented by Chemical Formula 1-1 or 1-2.

Chemical Formula 1-1

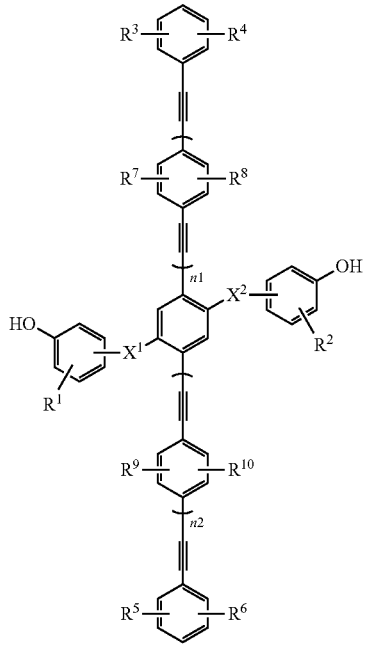

Chemical Formula 1-2

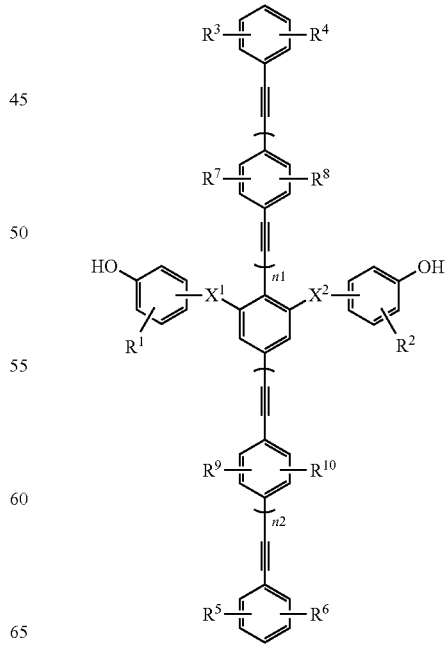

in Chemical Formula 1-1 and 1-2, $X^1$ and $X^2$ are independently O, C(=O), or C(=O)O, $R^1$ to $R^{10}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and n1 and n2 are independently an integer ranging from 0 to 3.

The monomer may be represented by one of Chemical Formula 1-1A to 1-2D.

Chemical Formula 1-1A

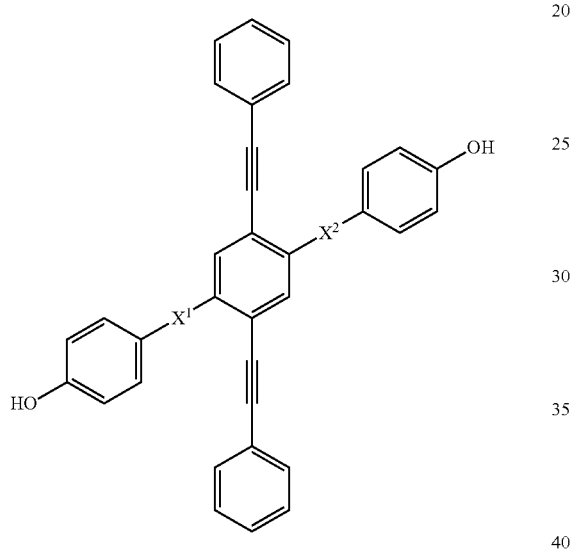

Chemical Formula 1-1B

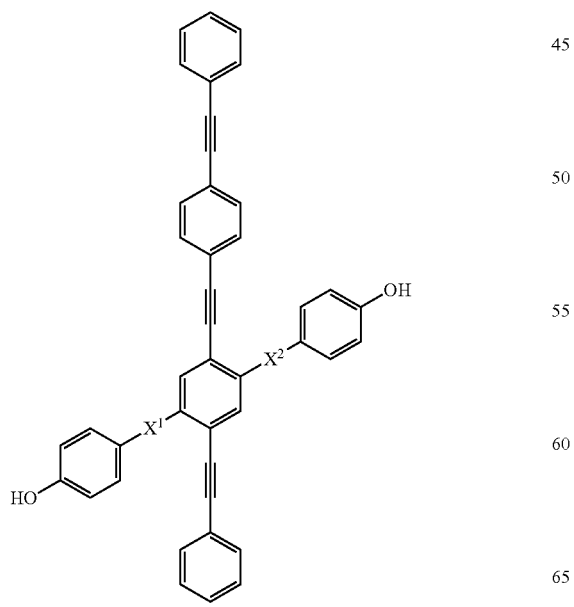

Chemical Formula 1-1C

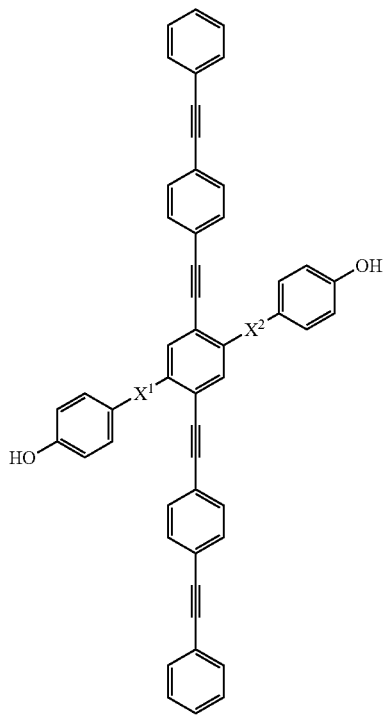

Chemical Formula 1-2A

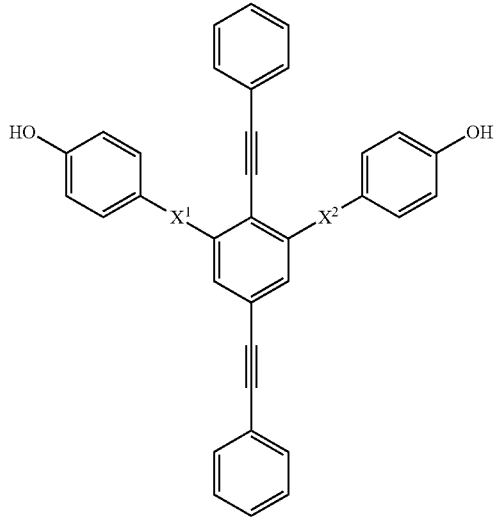

Chemical Formula 1-2B

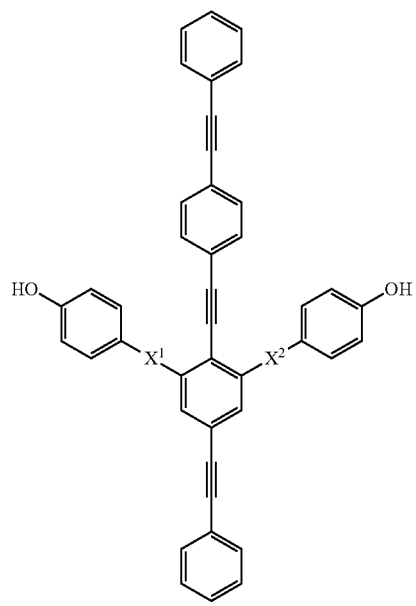

Chemical Formula 1-2C

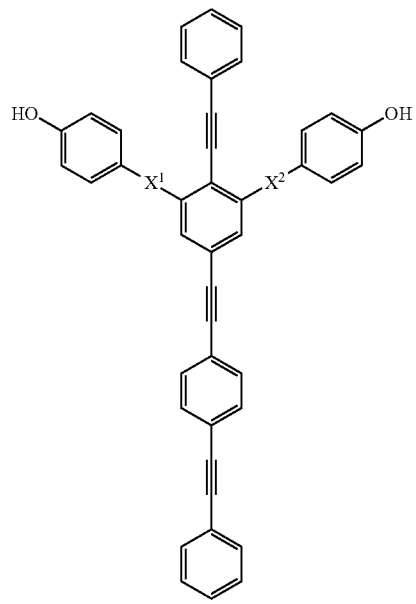

Chemical Formula 1-2D

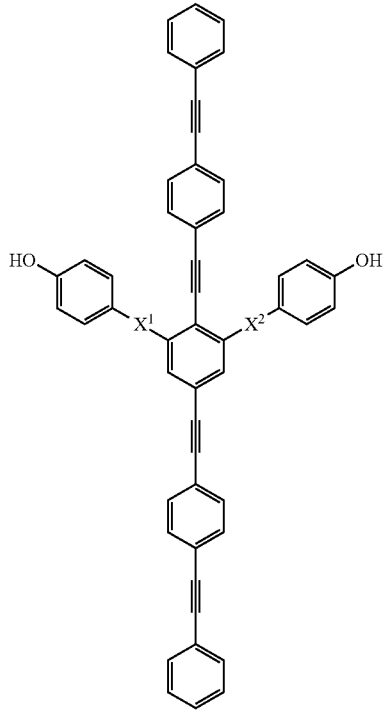

In Chemical Formula 1-1A to 1-2D,
$X^1$ and $X^2$ are independently O, C(=O), or C(=O)O.

According to another embodiment, a polymer having a structural unit derived from the monomer is provided.

The structural unit may be derived from a reaction product of the monomer with a carbonate or a derivative thereof.

According to another embodiment, a polymer having a first structural unit represented by Chemical Formula 3 is provided.

Chemical Formula 3

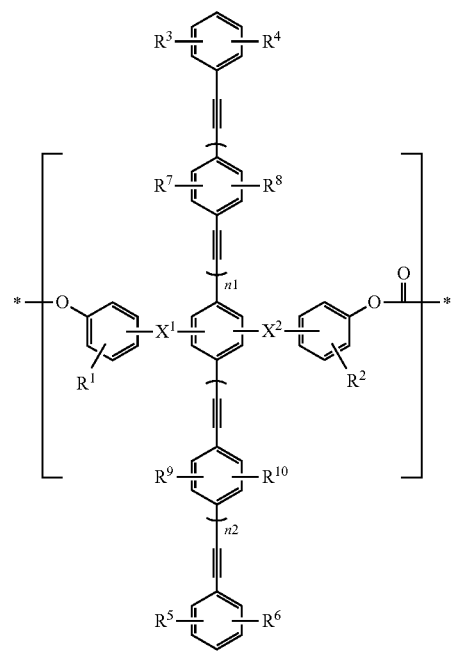

In Chemical Formula 3, $X^1$ and $X^2$ are independently O, C(=O), or C(=O)O, $R^1$ to $R^{10}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and n1 and n2 are independently an integer ranging from 0 to 3.

The first structural unit may be represented by Chemical Formula 3-1 or 3-2.

Chemical Formula 3-1

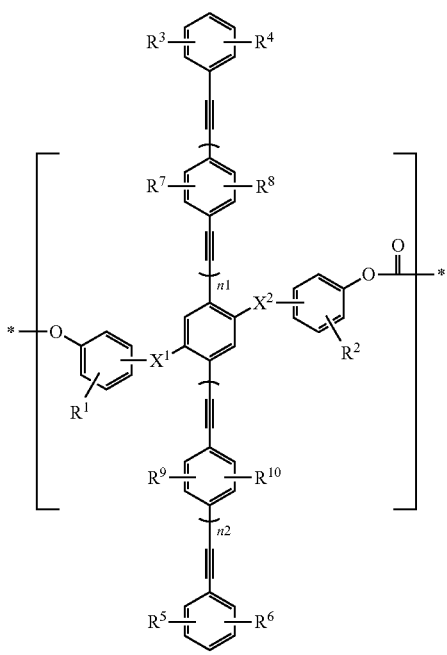

Chemical Formula 3-2

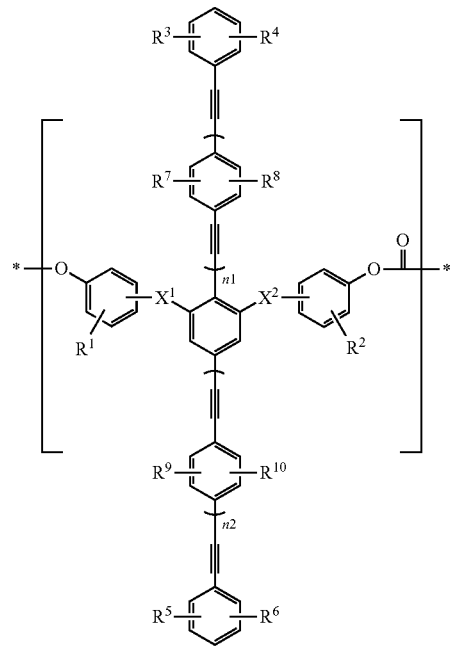

In Chemical Formula 3-1 and 3-2, $X^1$ and $X^2$ are independently O, C(=O), or C(=O)O, $R^1$ to $R^{10}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and n1 and n2 are independently an integer ranging from 0 to 3.

The first structural unit may be represented by one of Chemical Formula 3-1A to 3-2D.

Chemical Formula 3-1A

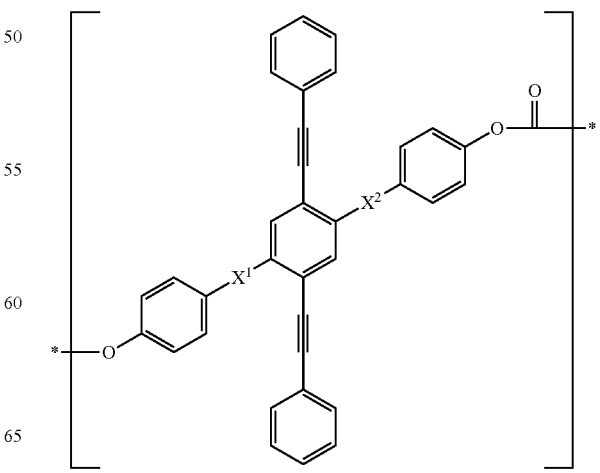

Chemical Formula 3-1B
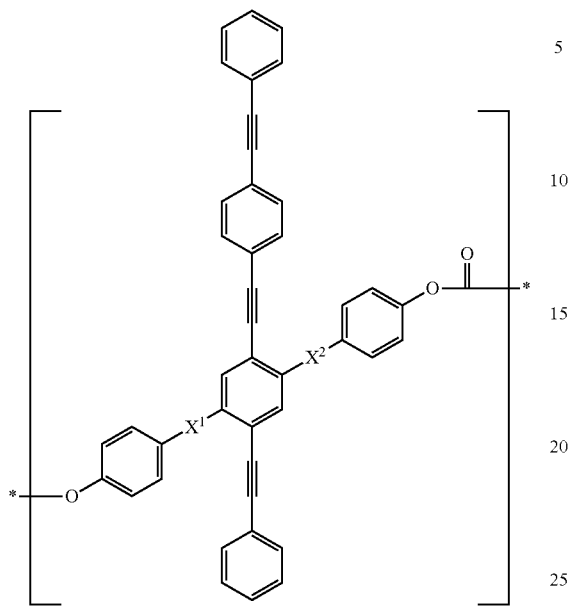
Chemical Formula 3-1C
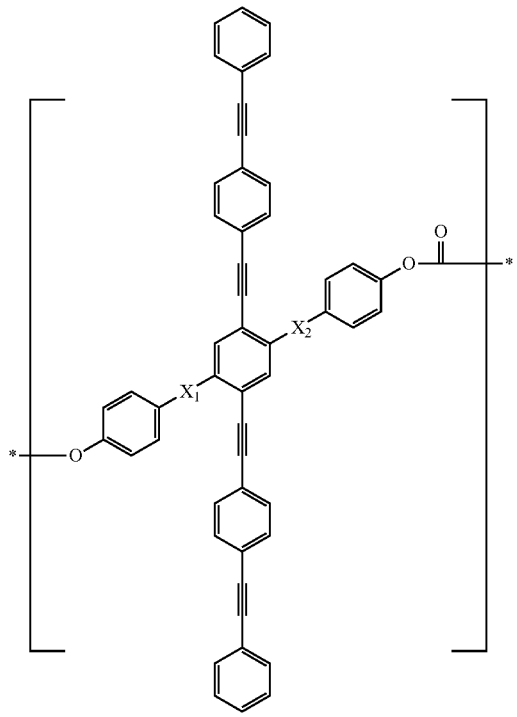
Chemical Formula 3-2A
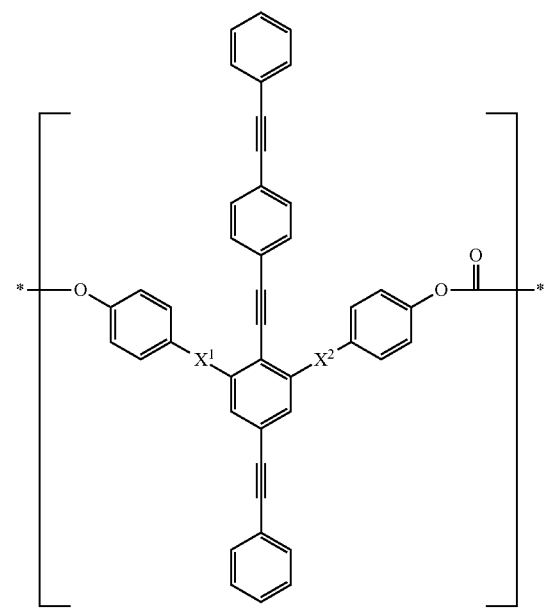
Chemical Formula 3-2B Chemical Formula 3-2C

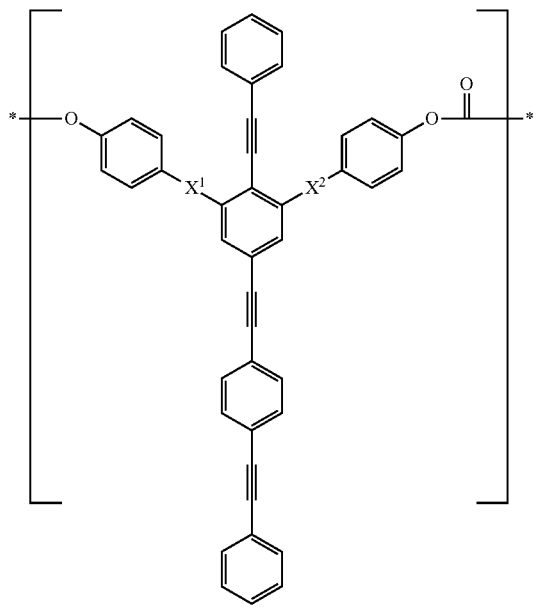

Chemical Formula 3-2D

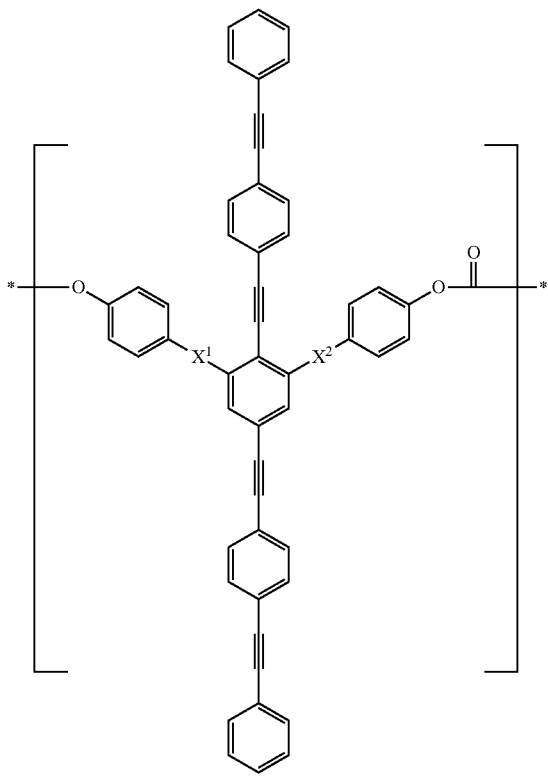

In Chemical Formula 3-1A to 3-2D,
$X^1$ and $X^2$ are independently O, C(=O), or C(=O)O.
The polymer may further include a second structural unit represented by Chemical Formula 4.

Chemical Formula 4

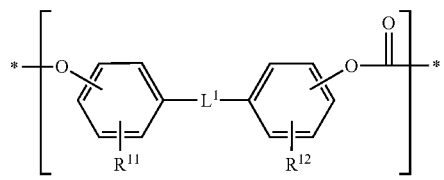

In Chemical Formula 4,
$L^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, O, C(=O), C(=O)O, $SO_2$, or a combination thereof, and $R^{11}$ and $R^{12}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof.

A mole ratio of the first structural unit and the second structural unit may be about 0.1:99.9 to about 10.0:90.0.

A mole ratio of the first structural unit and the second structural unit may be about 1:99 to about 5:95.

According to another embodiment, a compensation film includes a polymer having a structural unit derived from the monomer.

The structural unit may be derived from a reaction product of the monomer with a carbonate or a derivative thereof.

The compensation film may be elongated in a uniaxial or biaxial direction.

According to another embodiment, a compensation film includes a first polymer having the first structural unit represented by Chemical Formula 3.

The first structural unit may be represented by Chemical Formula 3-1 or 3-2.

The first structural unit may be represented by one of Chemical Formula 3-1A to 3-2D.

The first polymer may further include a second structural unit represented by Chemical Formula 4.

The first polymer may include the first structural unit and the second structural unit in a mole ratio of about 0.1:99.9 to about 10.0:90.0.

The first polymer may include the first structural unit and the second structural unit in a mole ratio of about 1:99 to about 5:95.

The compensation film may further include a second polymer having a structural unit represented by Chemical Formula 5.

Chemical Formula 5

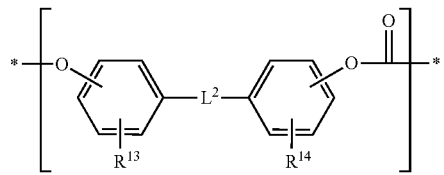

In Chemical Formula 5, $L^2$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, O, C(=O), C(=O)O, SO$_2$, or a combination thereof, and $R^{13}$ and $R^{14}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof.

The compensation film may include the first polymer and the second polymer in a mole ratio of about 1:9 to about 3:7.

The compensation film may be elongated in a uniaxial or biaxial direction.

Retardation values at 450 nanometer wavelength, 550 nanometer wavelength, and 650 nanometer wavelength of the compensation film may satisfy one of Relationship Equation 1 to 5.

$$R(450\ nm) \geq R(550\ nm) > R(650\ nm) \quad \text{Relationship Equation 1}$$

$$R(450\ nm) > R(550\ nm) \geq R(650\ nm) \quad \text{Relationship Equation 2}$$

$$R(450\ nm) = R(550\ nm) = R(650\ nm) \quad \text{Relationship Equation 3}$$

$$R(450\ nm) \leq R(550\ nm) < R(650\ nm) \quad \text{Relationship Equation 4}$$

$$R(450\ nm) < R(550\ nm) \leq R(650\ nm) \quad \text{Relationship Equation 5}$$

In Relationship Equations 1 to 5,

R(450 nm) is in-plane retardation or thickness direction retardation at a 450 nanometer wavelength, R(550 nm) is in-plane retardation or thickness direction retardation at a 550 nanometer wavelength, and R(650 nm) is in-plane retardation or thickness direction retardation at a 650 nanometer wavelength.

According to another embodiment, an optical film includes the compensation film and a polarizer.

According to another embodiment, a display device includes the compensation film or the optical film.

BRIEF DESCRIPTION OF THE DRAWINGS

These and/or other aspects will become apparent and more readily appreciated from the following description of the embodiments, taken in conjunction with the accompanying drawings, in which.

DETAILED DESCRIPTION

Figure 1:
FIG. 1 is a schematic cross-sectional view showing an optical film according to an embodiment.

Exemplary embodiments of the present disclosure will hereinafter be described in detail, and may be readily performed by person having an ordinary skill in the related art. However, this disclosure may be embodied in many different forms, and is not construed as limited to the exemplary embodiments set forth herein.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

As used herein, when a definition is not otherwise provided, the term "substituted" refers to a group or atom substituted with at least one substituent selected from a halogen, a hydroxy group, an alkoxy group, a nitro group, a cyano group, an amino group, an azido group, an amidino group, a hydrazino group, a hydrazono group, a carbonyl group, a carbamoyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof, instead of hydrogen of a compound.

As used herein, when a definition is not otherwise provided, the term "alkyl group" refers to a group derived from a straight or branched chain saturated aliphatic hydrocarbon having the specified number of carbon atoms and having a valence of at least one.

As used herein, when a definition is not otherwise provided, the term "alkoxy group" refers to "alkyl-O—", wherein the term "alkyl" has the same meaning as described above.

As used herein, when a definition is not otherwise provided, the term "cycloalkyl group" refers to a monovalent group having one or more saturated rings in which all ring members are carbon.

As used herein, when a definition is not otherwise provided, the term "aryl", which is used alone or in combination, refers to an aromatic hydrocarbon containing at least one ring and having the specified number of carbon atoms. The term "aryl" may be construed as including a group with an aromatic ring fused to at least one cycloalkyl ring.

As used herein, when a definition is not otherwise provided, the term "heterocyclic group" refers to a monovalent group having one or more saturated rings including one to three heteroatom ring members selected from the group consisting of N, O, S, Se, and P, wherein the remaining ring members are carbon.

As used herein, when a definition is not otherwise provided, the term "heterocyclic group" refers to a groups having formula —SiR$_3$, wherein R is each independently selected from an alkyl group and an aryl group as defined above.

As used herein, when a definition is not otherwise provided, the term "halogen" refers to fluorine, chlorine, bromine, and iodine.

As used herein, when a definition is not otherwise provided, the term "hydroxy group" refers to "—OH".

As used herein, when a definition is not otherwise provided, the term "nitro group" refers to "—NO$_2$".

As used herein, the term "alkylene group" refers to a straight or branched saturated aliphatic hydrocarbon group having a valence of at least two, optionally substituted with one or more substituents where indicated, provided that the valence of the alkylene group is not exceeded.

As used herein, the term "cycloalkylene group" refers to a cyclic hydrocarbon group having a valence of at least two, optionally substituted with one or more substituents where indicated, provided that the valence of the cycloalkylene group is not exceeded.

As used herein, when a definition is not otherwise provided, the term "arylene group" refers to a functional group having a valence of at least two obtained by removal of two hydrogens in an aromatic ring, optionally substituted with one or more substituents where indicated, provided that the valence of the alkylene group is not exceeded.

As used herein, the term "divalent heterocyclic group" refers to a cyclic group having a valence of at least two, optionally substituted with one or more substituents where indicated, and including one to three heteroatom ring members selected from the group consisting of N, O, S, Se, and P, wherein the remaining ring members are carbon, provided that the valence of the divalent heterocyclic group is not exceeded.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted C1-C30 alkyl" refers to a C1-C30 alkyl group substituted with C6-C30 aryl group, the total number of carbon atoms in the resulting aryl substituted alkyl group is C7-C60.

As used herein, when a definition is not otherwise provided, the term "hetero" refers to one including 1 to 3 hetero atoms selected from N, O, S, Se, and P.

Hereinafter, a monomer according to an embodiment is described.

A monomer according to an embodiment is represented by Chemical Formula 1.

Chemical Formula 1

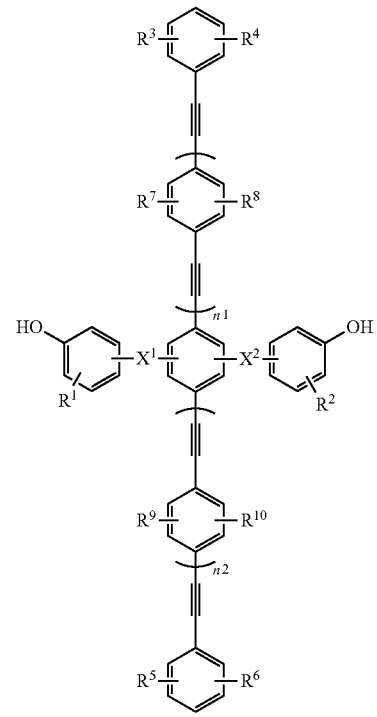

In Chemical Formula 1, $X^1$ and $X^2$ are independently O, C(=O), or C(=O)O, $R^1$ to $R^{10}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and n1 and n2 are independently an integer ranging from 0 to 3.

The monomer has a phenylacetylene group that is consecutively linked in one direction, and may effectively absorb light in a predetermined wavelength region due to the presence of the phenylacetylene group. Accordingly, it may be utilized in various devices requiring good optical properties.

For example, the monomer may react with an aliphatic or aromatic mesogen compound and may be used as a liquid crystal material having desirable optical properties.

For example, the monomer may react with a carbonate or a derivative thereof such as triphosgene to form a polycarbonate. The polycarbonate film may be, for example used as a compensation film having desirable optical properties.

In addition, the monomer may have improved solubility and may be synthesized relatively easily.

For example, in Chemical Formula 1, $X^1$ and $X^2$ may be the same or different.

For example, in Chemical Formula 1, n1 and n2 may independently be 0.

For example, in Chemical Formula 1, n1 and n2 may independently be 0 or 1.

The monomer may be, for example represented by Chemical Formula 1-1 or 1-2.

Chemical Formula 1-1

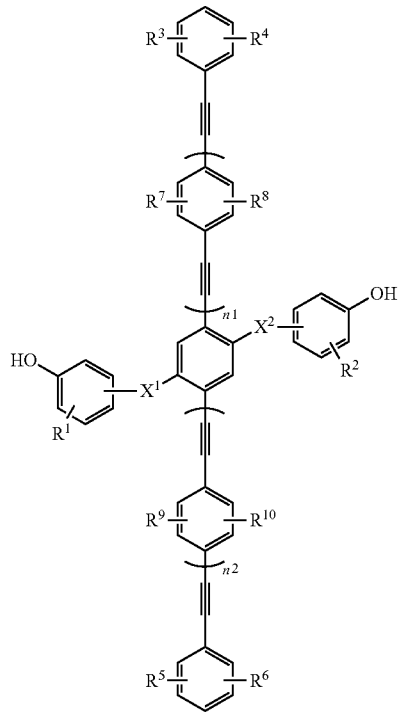

Chemical Formula 1-2

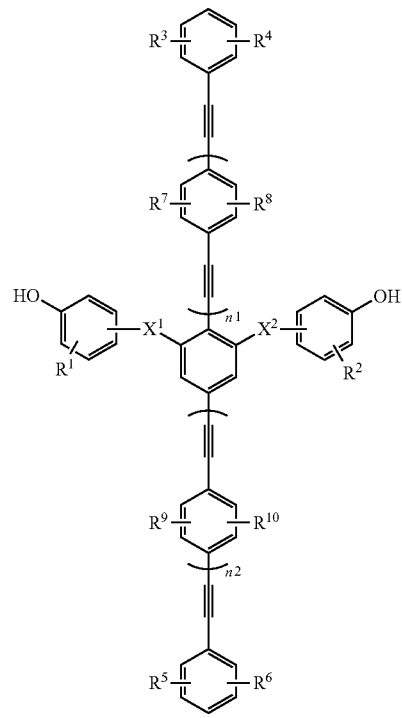

In Chemical Formula 1-1 and 1-2, $X^1$, $X^2$, $R^1$ to $R^{10}$, n1, and n2 are the same as described above.

For example, in Chemical Formula 1-1 or 1-2, $X^1$ and $X^2$ may be the same or different.

For example, in Chemical Formula 1-1 or 1-2, n1 and n2 may independently be 0.

For example, in Chemical Formula 1-1 or 1-2, n1 and n2 may independently be 0 or 1.

The monomer may be, for example, represented by one of Chemical Formula 1-1A to 1-2D, but is not limited thereto.

Chemical Formula 1-1A

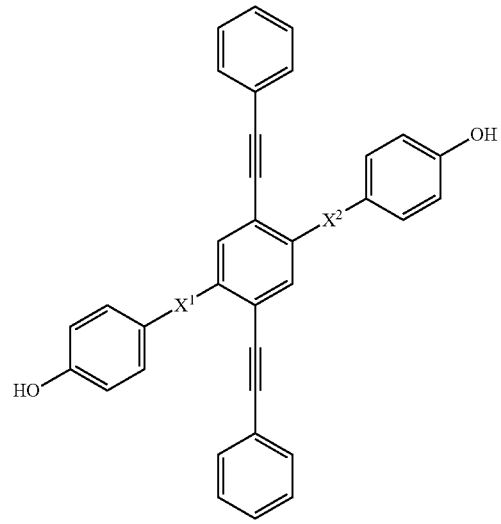

Chemical Formula 1-1B
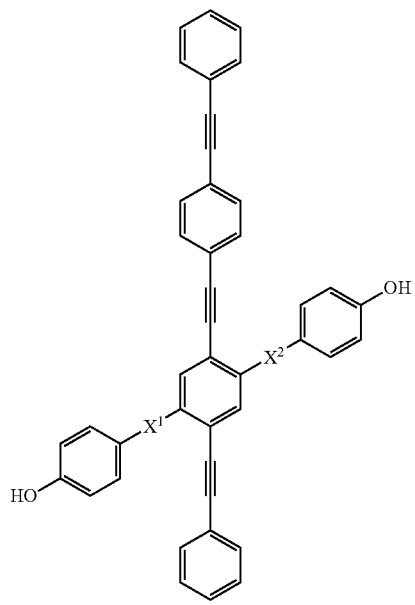
Chemical Formula 1-1C
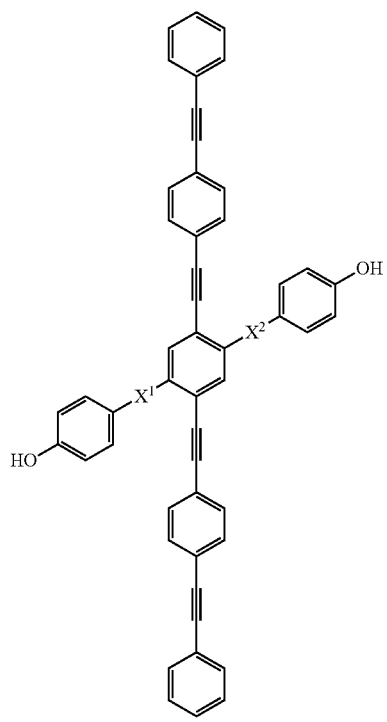
Chemical Formula 1-2A
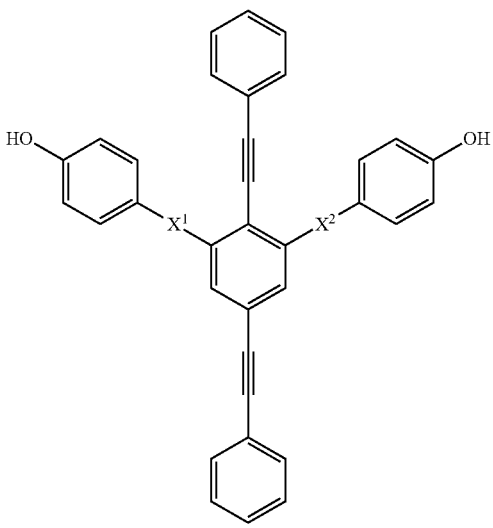
Chemical Formula 1-2B
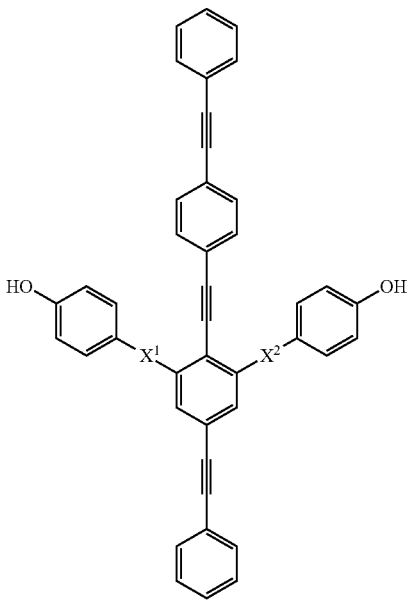

Chemical Formula 1-2C

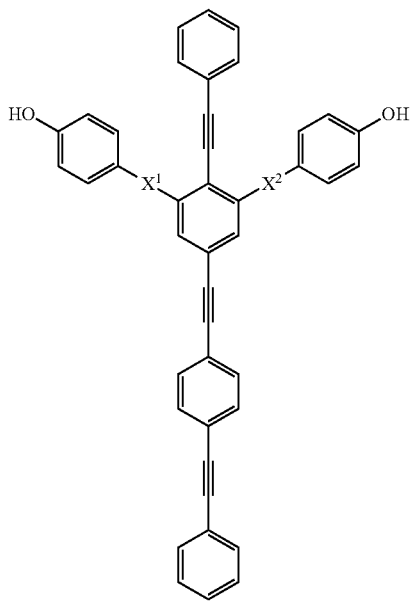

Chemical Formula 1-2D

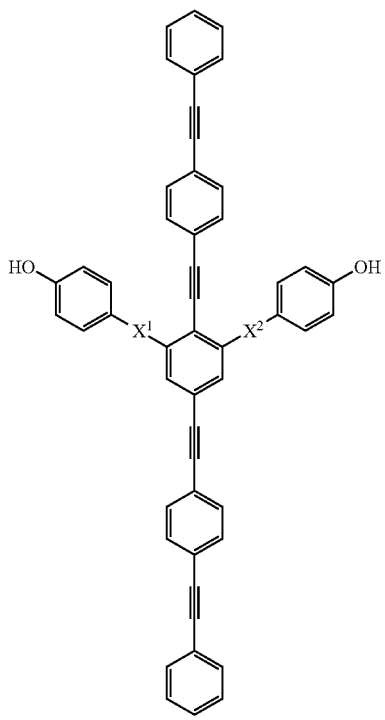

In Chemical Formula 1-1A to 1-2D, $X^1$ and $X^2$ are independently O, C(=O), or C(=O)O.

The monomer may form a homopolymer or a copolymer with other monomer. The polymer may have a structural unit derived from the monomer represented by Chemical Formula 1.

The monomer may react with a carbonate or a derivative thereof during polymerization to form a polycarbonate including a structural unit derived from the monomer represented by Chemical Formula 1.

The polymer may include a first structural unit represented by Chemical Formula 3.

Chemical Formula 3

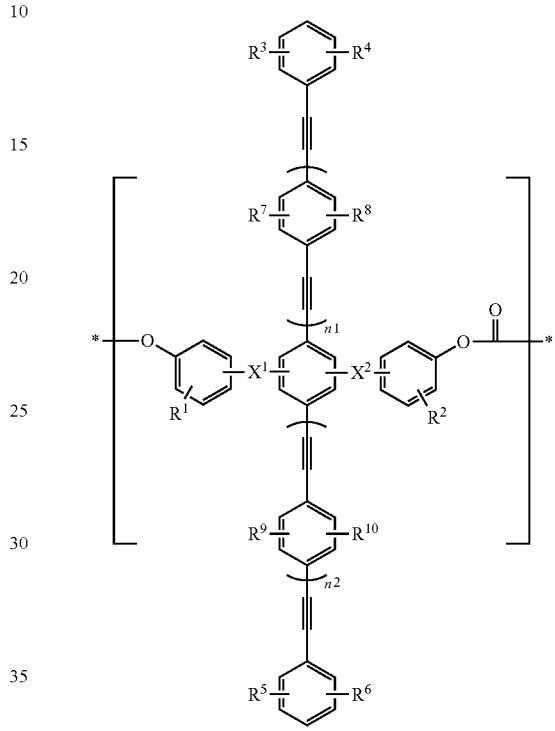

In Chemical Formula 3, $X^1$ and $X^2$ are independently O, C(=O), or C(=O)O, $R^1$ to $R^{10}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and n1 and n2 are independently an integer ranging from 0 to 3.

The first structural unit may include a main chain moiety obtained by a reaction of the monomer with a carbonate or a derivative thereof and a phenylacetylene group arranged with respect to a main chain moiety in a substantially perpendicular direction. The phenylacetylene group may be positioned at both sides of the main chain of the polymer symmetrically or asymmetrically, and a refractive index and light absorption characteristics depending on a wavelength may be changed by controlling the positions and the numbers of the phenylacetylene group. Accordingly, the polymer may be utilized in various fields that need good optical properties. For example, the polymer may control birefringence depending on a wavelength by varying a refractive index in a main chain direction and a refractive index in an arrangement direction of the phenylacetylene group.

The first structural unit may be, for example represented by Chemical Formula 3-1 or 3-2.

Chemical Formula 3-1

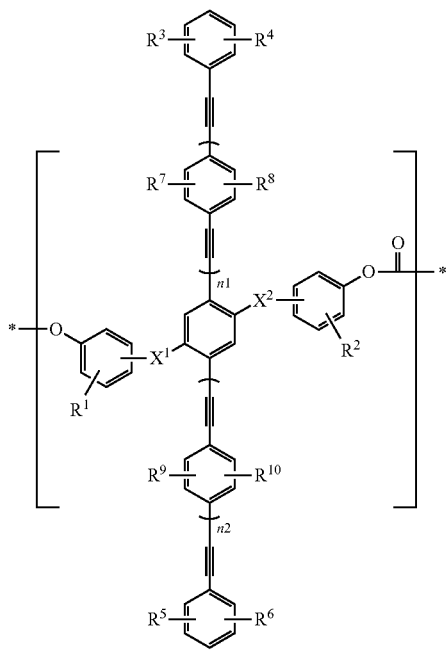

Chemical Formula 3-2

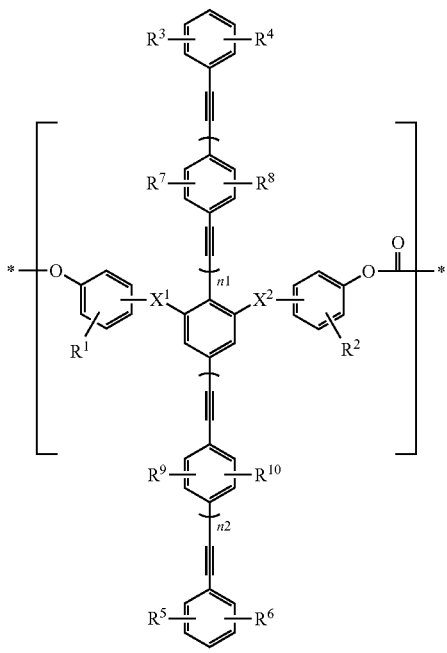

In Chemical Formula 3-1 and 3-2, $X^1$, $X^2$, $R^1$ to $R^{10}$, n1, and n2 are the same as described above.

For example, in Chemical Formula 3-1 or 3-2, $X^1$ and $X^2$ may be the same or different.

For example, in Chemical Formula 3-1 or 3-2, n1 and n2 may independently be 0.

For example, in Chemical Formula 3-1 or 3-2, n1 and n2 may independently be 0 or 1.

The first structural unit may be, for example represented by one of Chemical Formula 3-1A to 3-2D, but is not limited thereto.

Chemical Formula 3-1A

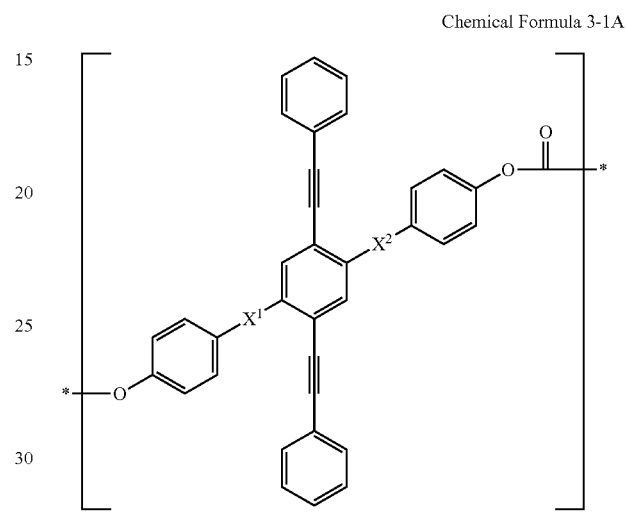

Chemical Formula 3-1B

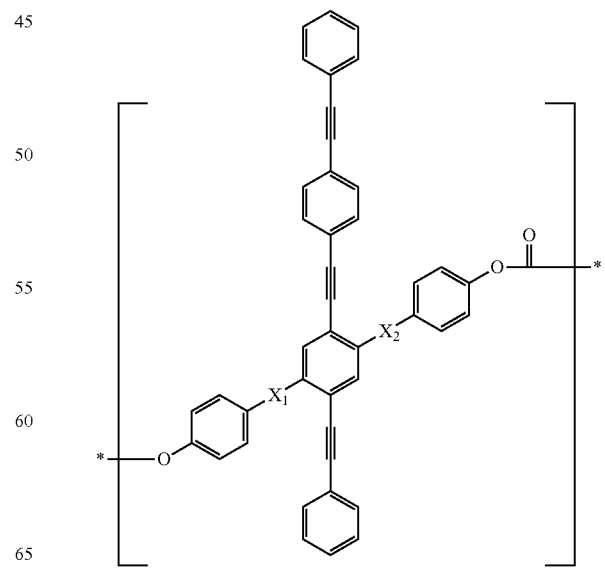

-continued
Chemical Formula 3-1C
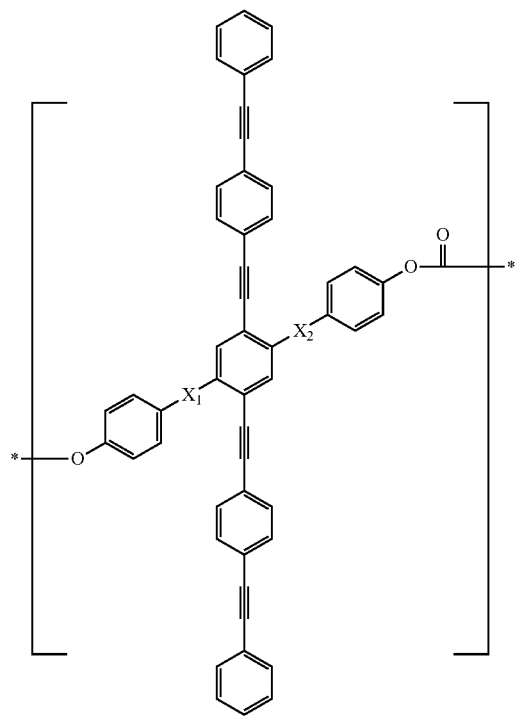
Chemical Formula 3-2A
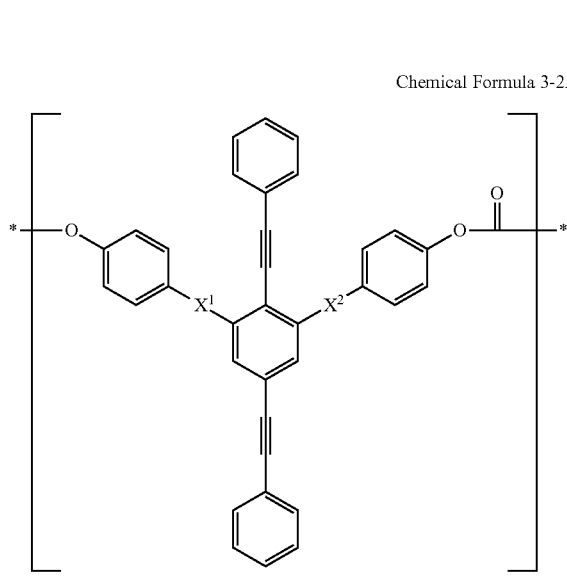
Chemical Formula 3-2B
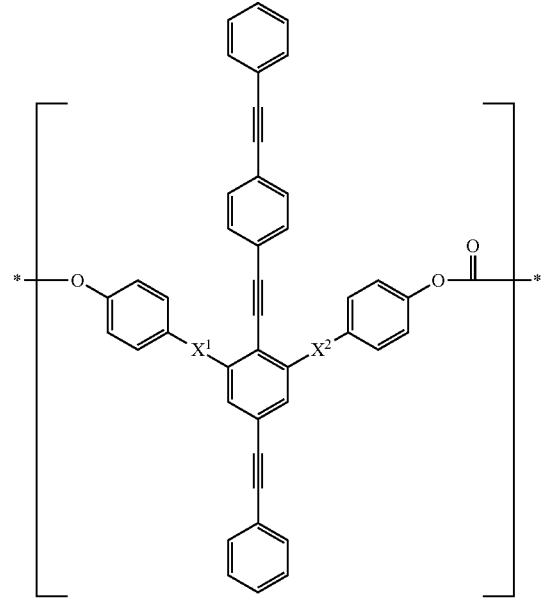
Chemical Formula 3-2C
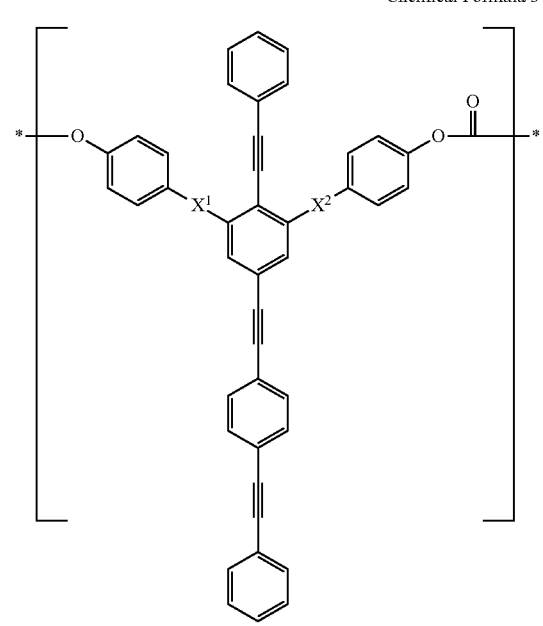

-continued

Chemical Formula 3-2D

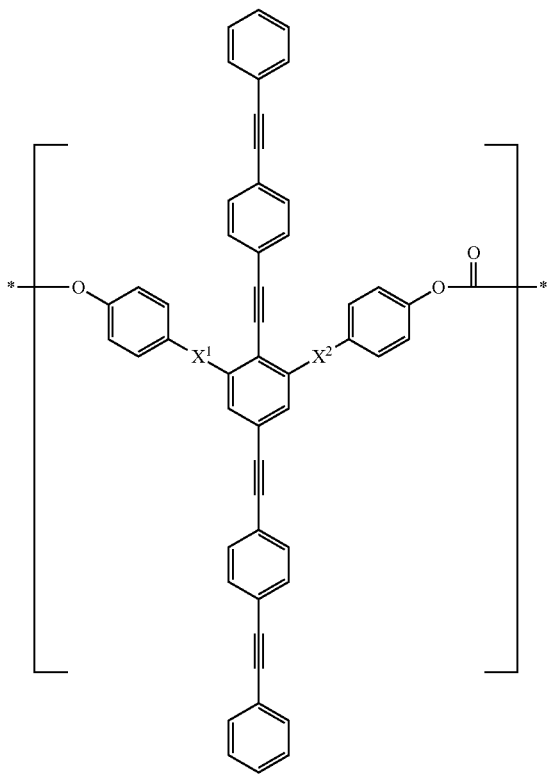

In Chemical Formula 3-1A to 3-2D, $X^1$ and $X^2$ are independently O, C(=O), or C(=O)O.

The polymer may be obtained by copolymerizing at least one other monomer in addition to the monomer represented by Chemical Formula 1, and may further include at least one structural unit derived from the at least one other monomer. The other monomer may react with the carbonate or the derivative thereof during polymerization to have a reaction site capable of forming a polycarbonate having a carbonate group. The other monomer may be, for example a monomer having a hydroxy group, and may be, for example bisphenol or a derivative thereof, but is not limited thereto.

For example, when the bisphenol or the derivative thereof is polymerized together, the polymer may further include a second structural unit represented by Chemical Formula 4.

Chemical Formula 4

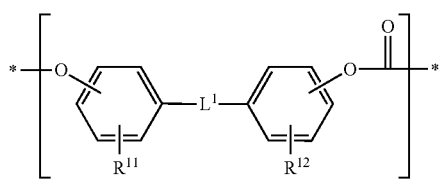

In Chemical Formula 4, $L^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, O, C(=O), C(=O)O, SO$_2$, or a combination thereof, and $R^{11}$ and $R^{12}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof.

The second structural unit may have a main chain moiety obtained by a reaction of the bisphenol or a derivative thereof with the carbonate or a derivative thereof.

When the first polymer includes the first structural unit and the second structural unit, the first structural unit and the second structural unit may be included in a mole ratio of about 0.1:99.9 to about 10.0:90.0. While not wishing to be bound by theory, it is understood that within the above ranges, flexibility may be improved and the desirable optical properties may be obtained, and thus the polymer may be readily transformed into a film. While not wishing to be bound by theory, it is understood that within the above ranges, the first and second structural units may be, for example, included in a mole ratio of about 0.5:99.5 to about 10:90, or about 1:99 to about 5:95.

The polymer may be, for example prepared in a form of a film, and thus may be used as a polymer film. The polymer film may be, for example transparent, and thus may be used in any device that needs transparency. The polymer film may be used for various applications, for example a substrate, a protective film, a compensation film, an optical film, a dielectric layer, an insulation layer, an adhesive layer, and the like.

Hereinafter, a compensation film according to an embodiment is described.

A compensation film according to an embodiment may include a first polymer that is a homopolymer of the monomer represented by Chemical Formula 1 or a copolymer with at least one other monomer. Accordingly, the first polymer may have a first structural unit derived from the monomer represented by Chemical Formula 1, and the first structural unit may be derived from a reaction of the monomer represented by Chemical Formula 1 with a carbonate or a derivative thereof.

The first polymer may include a first structural unit represented by Chemical Formula 3.

Chemical Formula 3

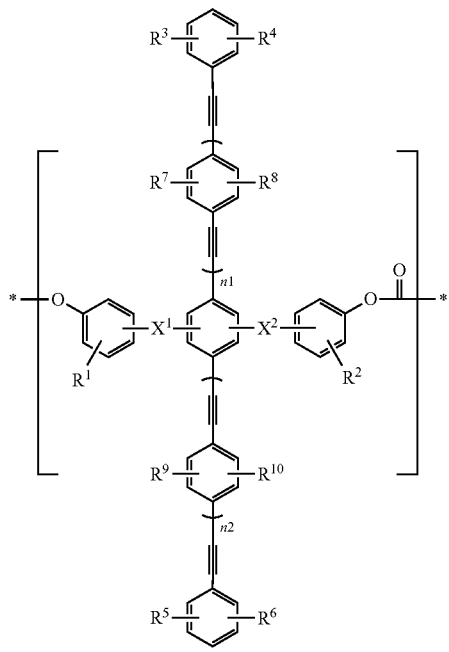

In Chemical Formula 3, $X^1$ and $X^2$ are independently O, C(=O), or C(=O)O, $R^1$ to $R^{10}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and n1 and n2 are independently an integer ranging from 0 to 3.

The first structural unit may include a main chain moiety obtained by a reaction of the monomer with a carbonate or a derivative thereof and a phenylacetylene group arranged with respect to a main chain in a substantially perpendicular direction. The phenylacetylene group may be positioned at both sides of the main chain of the polymer symmetrically or asymmetrically, and a refractive index and the first structural unit may change light absorption characteristics depending on a wavelength and may have retardation by controlling the positions and the numbers of the phenylacetylene group. For example, the first polymer may control birefringence depending on a wavelength by varying a refractive index in a main chain direction and a refractive index in an arrangement direction of the phenylacetylene group.

The first structural unit may be, for example represented by Chemical Formula 3-1 or 3-2.

Chemical Formula 3-1

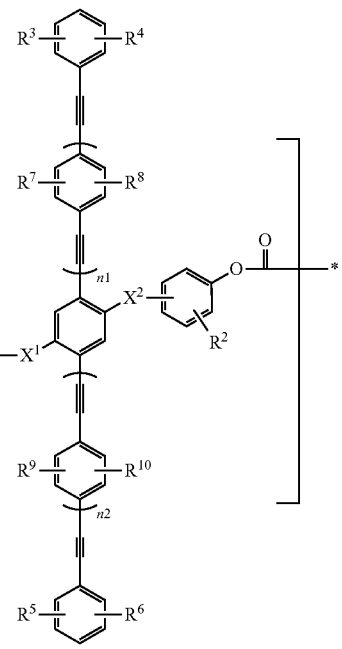

Chemical Formula 3-2

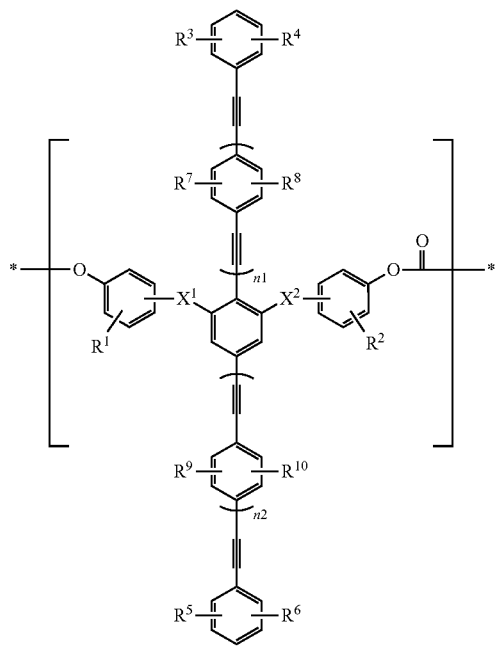

In Chemical Formula 3-1 and 3-2, $X^1$, $X^2$, $R^1$ to $R^{10}$, n1, and n2 are the same as described above.

For example, in Chemical Formula 3-1 or 3-2, $X^1$ and $X^2$ may be the same or different.

For example, in Chemical Formula 3-1 or 3-2, n1 and n2 may independently be 0.

For example, in Chemical Formula 3-1 or 3-2, n1 and n2 may independently be 0 or 1.

The first structural unit may be, for example represented by one of Chemical Formula 3-1A to 3-2D, but is not limited thereto.

Chemical Formula 3-1A
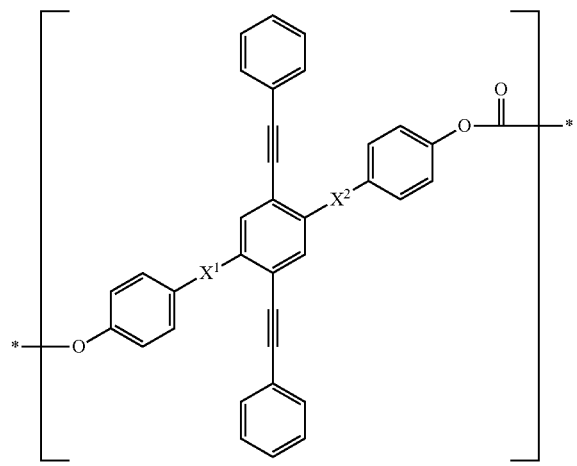
Chemical Formula 3-1B
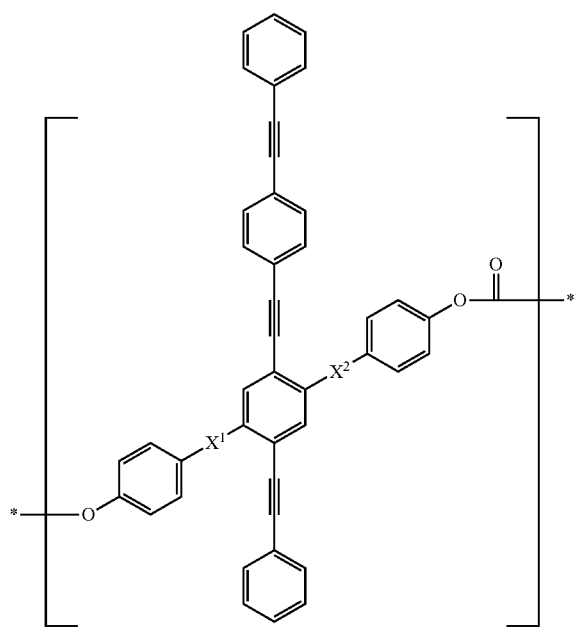
Chemical Formula 3-1C
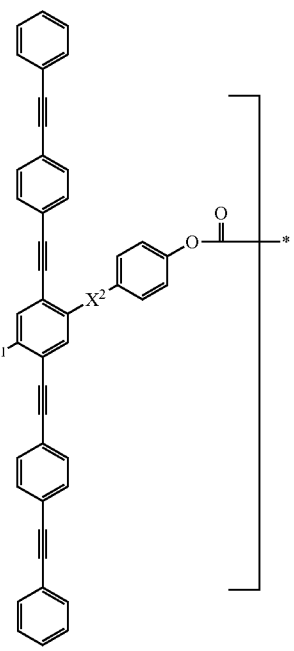
Chemical Formula 3-2A
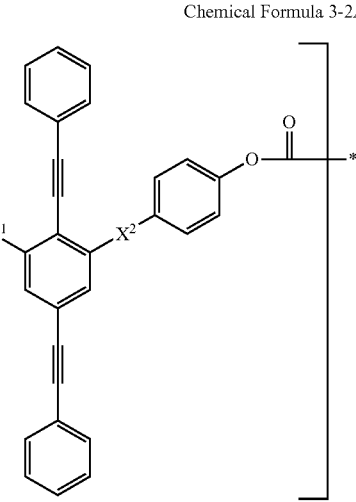

-continued

Chemical Formula 3-2B

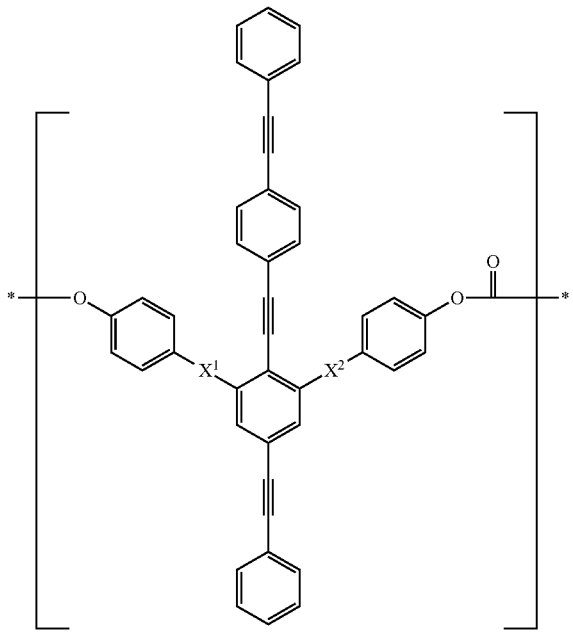

Chemical Formula 3-2C

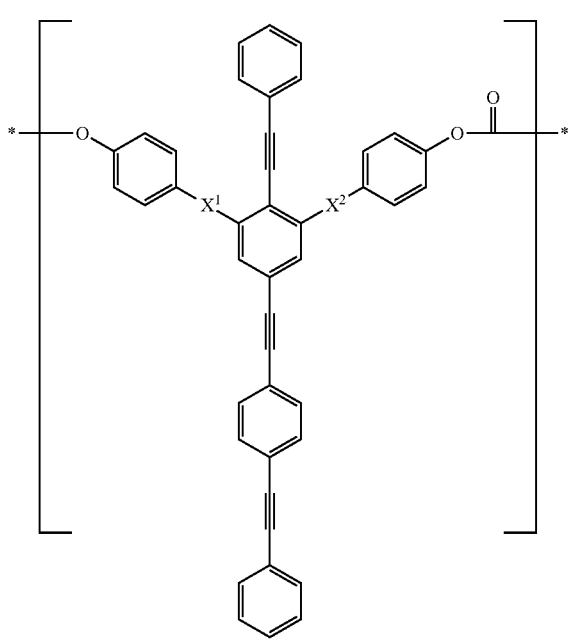

-continued

Chemical Formula 3-2D

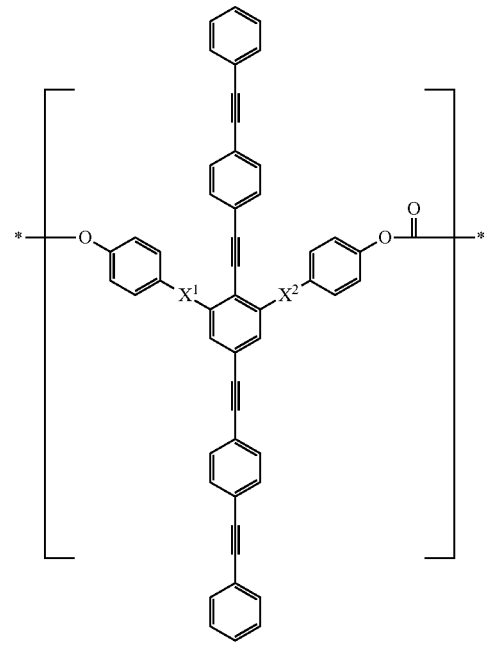

In Chemical Formula 3-1A to 3-2D, $X^1$ and $X^2$ are independently O, C(=O), or C(=O)O.

The first polymer may be obtained by copolymerizing at least one other monomer in addition to the monomer represented by Chemical Formula 1, and may further include at least one structural unit derived from the at least one other monomer. The at least one other monomer may react with the carbonate or the derivative thereof during polymerization to form a polycarbonate having a carbonate group. The other monomer may react with the carbonate or the derivative thereof during polymerization to have a reaction site capable of forming a polycarbonate having a carbonate group. The other monomer may be, for example a monomer having a hydroxy group, and may be, for example bisphenol or a derivative thereof, but is not limited thereto.

For example, when the bisphenol or the derivative thereof is polymerized together, the first polymer may further include a second structural unit represented by Chemical Formula 4.

Chemical Formula 4

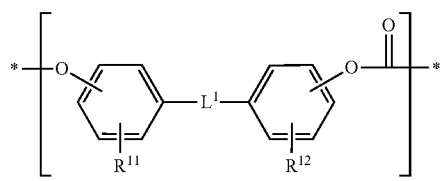

In Chemical Formula 4, $L^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, O, C(=O), C(=O)O, $SO_2$, or a combination thereof, and $R^{11}$ and $R^{12}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof.

The second structural unit may have a main chain moiety obtained by a reaction of the bisphenol or a derivative thereof with the carbonate or a derivative thereof.

When the first polymer includes the first structural unit and the second structural unit, the first structural unit and the second structural unit may be included in a mole ratio of about 0.1:99.9 to about 10.0:90.0. While not wishing to be bound by theory, it is understood that within the ranges, flexibility may be improved and the desirable optical properties may be obtained, and thus the polymer may be readily transformed into a film. While not wishing to be bound by theory, it is understood that within the above ranges, the first and second repeating units may be, for example, included in a mole ratio of about 0.5:99.5 to about 10:90, or about 1:99 to about 5:95.

The compensation film may further include at least one second polymer in addition to the first polymer. The compensation film may have further improved optical physical characteristics by including the second polymer.

The second polymer may be any polymer to make a function of the compensation film better and is not particularly limited, and may have, for example a structural unit having a substituted or unsubstituted arylene group and a carbonate group.

The second polymer may have, for example a structural unit represented by Chemical Formula 5.

Chemical Formula 5

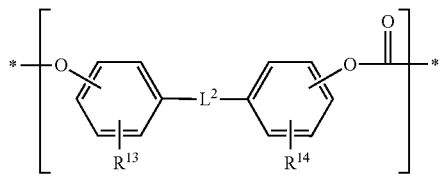

In Chemical Formula 5, $L^2$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, O, C(=O), C(=O)O, $SO_2$, or a combination thereof, and $R^{13}$ and $R^{14}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof.

The first polymer and the second polymer may be included, for example in a mole ratio of about 1:9 to about 9:1, for example about 1:9 to about 2:8, or about 1:9 to about 3:7. While not wishing to be bound by theory, it is understood that within these ranges, flexibility may be improved and the desirable optical properties may be obtained, and thus the polymer may be readily transformed into a film.

The compensation film may be, for example elongated in a uniaxial or biaxial direction. For example, the compensation film may be elongated in a uniaxial direction.

As described above, the compensation film may have a predetermined retardation, which may be obtained by changing a refractive index and light absorption characteristics depending on a wavelength.

Retardation (R) of the compensation film may be expressed as an in-plane retardation ($R_o$) and a thickness direction retardation ($R_{th}$). The in-plane retardation ($R_o$) of the compensation film is a retardation generated in an in-plane direction of the compensation film and represented by the equation $R_o=(n_x-n_y)d$. The thickness direction retardation ($R_{th}$) of the compensation film is a retardation of the compensation film generated in a thickness direction and is represented by the equation $R_{th}=\{[(n_x+n_y)/2]-n_z\}d$. Herein, $n_x$ is a refractive index in a direction having a highest refractive index in a plane of a compensation film (hereinafter referred to as 'slow axis'), $n_y$ is a refractive index in a direction having a lowest refractive index in a plane of the compensation film (hereinafter referred to as 'fast axis'), $n_z$ is a refractive index in a direction perpendicular to the slow axis and the fast axis of a compensation film, and d is a thickness of a compensation film.

The compensation film may have an in-plane retardation and a thickness direction retardation within a predetermined range by changing the $n_x$, $n_y$, $n_z$, and/or the thickness (d).

The compensation film may have the same or different retardation depending on a wavelength.

For example, the compensation film may have a forward wavelength dispersion phase delay where a retardation of light at a shorter wavelength is larger than a retardation of light at a longer wavelength. When a 550 nanometer (nm) wavelength is a reference wavelength, for example retardation values (R) at 450 nm wavelength, 550 nm wavelength, and 650 nm wavelength of the compensation film may satisfy Relationship Equation 1 or 2.

$R(450 \text{ nm}) \geq R(550 \text{ nm}) > R(650 \text{ nm})$      Relationship Equation 1

$R(450 \text{ nm}) > R(550 \text{ nm}) \geq R(650 \text{ nm})$      Relationship Equation 2

For example, the compensation film may have a flat dispersion phase delay where a retardation of light at a longer wavelength and a retardation of light at a shorter wavelength are substantially equivalent. For example retardation values (R) in 450 nm wavelength, 550 nm wavelength, and 650 nm wavelength of the compensation film may satisfy Relationship Equation 3.

$R(450 \text{ nm}) = R(550 \text{ nm}) = R(650 \text{ nm})$      Relationship Equation 3

For example, the compensation film may have a reverse wavelength dispersion phase delay where a retardation of light at a longer wavelength is larger than a retardation of light at a shorter wavelength. For example retardation values (R) at 450 nm wavelength, 550 nm wavelength, and 650 nm wavelength of the compensation film may satisfy Relationship Equation 4 or 5.

$R(450 \text{ nm}) \leq R(550 \text{ nm}) < R(650 \text{ nm})$      Relationship Equation 4

$R(450 \text{ nm}) < R(550 \text{ nm}) \leq R(650 \text{ nm})$      Relationship Equation 5

In Relationship Equations 1 to 5,

R(450 nm) is in-plane retardation or thickness direction retardation at a 450 nm wavelength, R(550 nm) is in-plane retardation or thickness direction retardation at a 550 nm wavelength, and R(650 nm) is in-plane retardation or thickness direction retardation at a 650 nm wavelength.

The desirable retardation of the compensation film may be obtained by varying a wavelength.

The compensation film may have a relatively low thickness due to high birefringence. The compensation film may have, for example a thickness of about 3 micrometers (μm) to about 200 μm, for example about 5 μm to about 150 μm, or about 5 μm to about 100 μm.

The compensation film includes a substantially transparent polymer, and thus may be used as a substrate. Accordingly, a separate substrate under the compensation film may be omitted. Thereby, a thickness of the compensation film may be further reduced. Accordingly, the compensation film may be suitable for application in a flexible display device such as a foldable display device or a bendable display device and may have improve optical properties and display characteristics.

The compensation film may be manufactured by a method including, for example preparing monomers, polymerizing the monomers to prepare a polymer, preparing the polymer in a form of a film, and elongating the film.

The compensation film may be, for example elongated at an elongation rate of about 110% to about 1,000% at a temperature of about 50° C. to about 500° C. The elongation rate refers to a length ratio of after the elongation to before the elongation of the compensation film, and is a measure of the elongation extent of the compensation film after uniaxial elongation.

The compensation film may be used alone or together with other compensation film.

The compensation film may be used with a polarizer which may be utilized as an optical film to prevent reflection of external light of a display device. The optical film may be, for example an antireflective film, but is not limited thereto.

Figure 2:
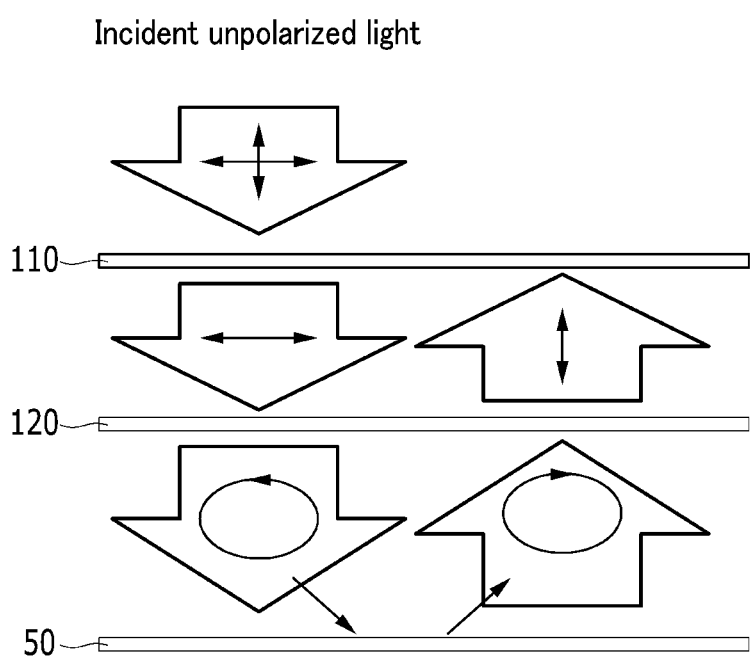
FIG. 2 is a schematic view showing the external light anti-reflection principle of an optical film.
Figure 3:
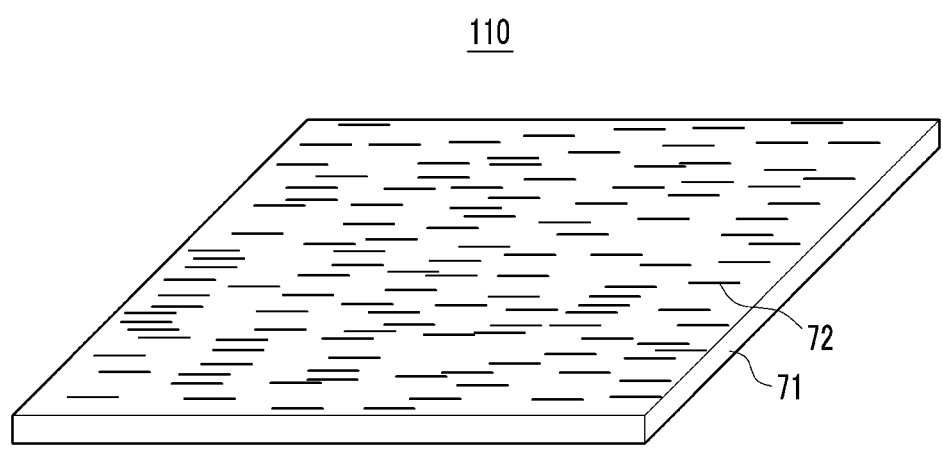
FIG. 3 is a schematic view of an example of a polarizing film.

FIG. 1 is a schematic cross-sectional view showing an optical film according to an embodiment, FIG. 2 is a schematic view showing the external light anti-reflection principle of an optical film, and FIG. 3 is a schematic view of an example of a polarizing film.

Referring to FIG. 1, an optical film 100 according to an embodiment includes a polarizer 110 and a compensation film 120. The compensation film 120 may circularly-polarize light passed through the polarizer 110 to generate retardation, and may influence reflection and/or absorption of light.

For example, the optical film 100 may be mounted on one side or both sides of the display device, and particularly, may prevent light from flowing into the display part of the display device from the outside (hereinafter referred to as "external light") from being reflected. Accordingly, the optical film 100 may prevent the visibility deterioration caused by the external light reflection.

FIG. 2 is a schematic view showing the external light anti-reflection principle of an optical film.

Referring to FIG. 2, while the incident unpolarized light having entered from the outside is passed through the polarizer 110, and the polarized light is shifted into circularly polarized light by passing through the compensation film 120, only a first polarized perpendicular component, which is one polarized perpendicular component of two polarized perpendicular components, is transmitted. While the circularly polarized light is reflected in a display panel 50 including a substrate, an electrode, and so on, and changes the circular polarization direction, and the circularly polarized light is passed through the compensation film 120 again, only a second polarized perpendicular component, which is the other polarized perpendicular component of the two polarized perpendicular components, may be transmitted. As the second polarized perpendicular component is not passed through the polarizer 110, and light is not present on the outside, effects of preventing the external light reflection may be provided.

The polarizer 110 may be, for example a polarizing plate or a polarization film.

Referring to FIG. 3, the polarizer 110 may be a self-integrated polarizing film made of, for example a melt blend of a polymer 71 and a dichroic dye 72.

The polymer 71 may be, for example a hydrophobic polymer, for example a polyolefin such as polyethylene (PE), polypropylene (PP), and a copolymer thereof; a polyamide such as nylon and aromatic polyamide; a polyester such as polyethylene terephthalate (PET), polyethylene terephthalate glycol (PETG), and polyethylene naphthalate (PEN); a polyacryl such as polymethyl(meth)acrylate; a polystyrene such as polystyrene (PS) and an acrylonitrile-styrene copolymer; a polycarbonate; a vinyl chloride polymer; a polyimide; a sulfone polymer; a polyethersulfone; a polyether-etherketone; a polyphenylene sulfide; a vinyl alcohol polymer; a vinylidene chloride polymer; a vinyl butyral polymer; an allylate polymer; a polyoxymethylene; epoxy, a copolymer thereof, or a combination thereof.

In an embodiment, the polymer 71 may be, for example a polyolefin, a polyamide, a polyester, a polyacrylic, a polystyrene, a copolymer thereof, or a combination thereof, and may be, for example polyethylene (PE), polypropylene (PP), polyethylene terephthalate (PET), polyethylene terephthalate glycol (PETG), polyethylene naphthalate (PEN), nylon, a copolymer thereof, or a combination thereof.

In an embodiment, the polymer 71 may be polyolefin. The polyolefin may be, for example a mixture of two or more selected from polyethylene (PE), polypropylene (PP), a copolymer of polyethylene and polypropylene (PE-PP), for example a mixture of polypropylene (PP) and a polyethylene-polypropylene copolymer (PE-PP).

The polymer 71 may have a transmittance of greater than or equal to about 85% in a wavelength region of about 400 nm to about 780 nm. The polymer 71 may be elongated in a uniaxial direction. The uniaxial direction may be the same as a length direction of the dichroic dye 72 which will be described later.

The dichroic dye 72 may be dispersed in the polymer 71, and may be aligned in the elongation direction of the polymer 71. The dichroic dye 72 transmits one perpendicular polarization component out of two perpendicular polarization components in a predetermined wavelength region.

The dichroic dye 72 may be included in an amount of about 0.01 to about 5 parts by weight based on 100 parts by weight of the polymer 71. While not wishing to be bound by theory, it is understood that within the above range, sufficient polarization characteristics may be obtained without deteriorating transmittance of a polarization film. Within the above range, the dichroic dye may be included in an amount of about 0.05 to about 1 part by weight based on 100 parts by weight of the polymer 71.

The polarizer 110 may have a relatively low thickness of less than or equal to about 100 μm, for example, for example about 30 μm to about 95 μm. While not wishing to be bound by theory, it is understood that when the polarizer 110 has a thickness with the above range, the polarizer 110 is relatively thinner than a polyvinyl alcohol polarizing plate requiring a protective layer such as triacetyl cellulose (TAC), and thus may realize a thin display device.

The compensation film 120 is the same as described above.

The optical film 100 may further include a correction layer (not shown) positioned on one side of the compensation film 120. The correction layer may be, for example, a color shift resistant layer, but is not limited thereto.

The optical film 100 may further include a light blocking layer (not shown) extended along the edge. The light blocking layer may be formed in a strip along the circumference of the optical film 100, and for example, may be positioned between the polarizer 110 and the compensation film 120. The light blocking layer may include an opaque material, for example, a black material. For example, the light blocking layer may be made of a black ink.

The optical film 100 may be applied to various display devices.

A display device according to an embodiment includes a display panel and an optical film positioned on one side of the display panel. The display panel may be a liquid crystal panel or organic light emitting panel, but is not limited thereto.

Hereinafter, an organic light emitting device is described as an example of a display device.

Figure 4:
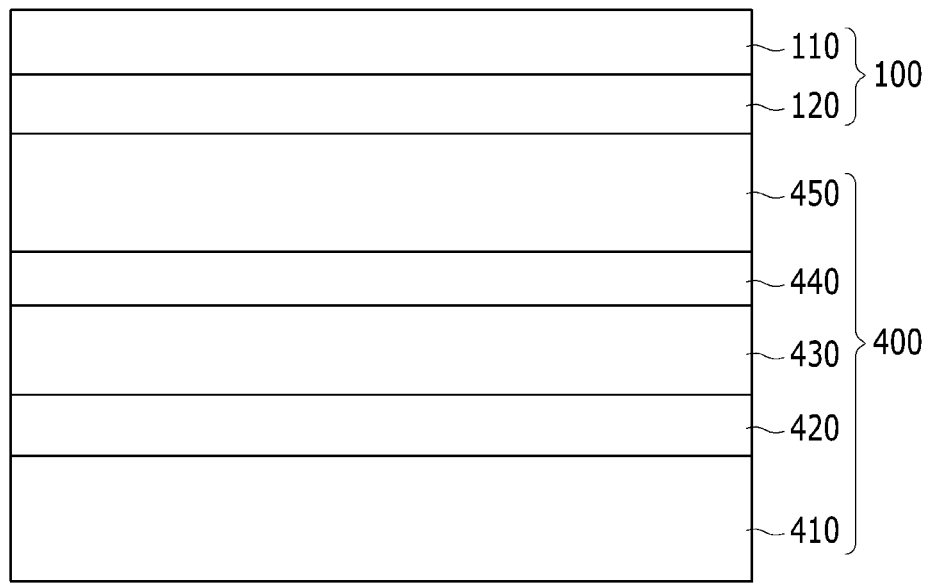
FIG. 4 is a schematic cross-sectional view showing an organic light emitting device according to an embodiment.

FIG. 4 is a schematic cross-sectional view showing an organic light emitting device according to an embodiment.

Referring to FIG. 4, the organic light emitting device according to an embodiment includes an organic light emitting panel 400 and an optical film 100 positioned on one side of the organic light emitting diode panel 400.

The organic light emitting diode panel 400 may include a base substrate 410, a lower electrode 420, an organic emission layer 430, an upper electrode 440, and an encapsulation substrate 450.

The base substrate 410 may be made of glass or plastic.

At least one of the lower electrode 420 and the upper electrode 440 may be an anode, and the other one may be a cathode. The anode is an electrode injected with holes, and may be made of a transparent conductive material having a high work function to transmit the emitted light to the outside, for example, ITO or IZO. The cathode is an electrode injected with electrons, and may be made of a conductive material having a low work function without affecting the organic material, and may be selected from, for example, aluminum (Al), calcium (Ca), and barium (Ba).

The organic emission layer 430 includes an organic material which may emit light when a voltage is applied to the lower electrode 420 and the upper electrode 440.

An auxiliary layer (not shown) may be further provided between the lower electrode 420 and the organic emission layer 430 and between the upper electrode 440 and the organic emission layer 430. The auxiliary layer is used to balance electrons and holes, and may include a hole transport layer, a hole injection layer (HIL), an electron injection layer (EIL), and an electron transporting layer.

The encapsulation substrate 450 may be made of glass, metal, or a polymer, and may seal the lower electrode 420, the organic emission layer 430, and the upper electrode 440 to prevent moisture and/or oxygen inflow from the outside.

The optical film 100 may be disposed on the light-emitting side. For example, when a bottom emission structure emits light at the side of the base substrate 410, the optical film 100 may be disposed on the exterior side of the base substrate 410. On the other hand, when a top emission structure emits light at the side of the encapsulation substrate 450, the optical film 100 may be disposed on the exterior side of the encapsulation substrate 450.

The optical film 100 includes the self-integrated polarizer 110 and the self-integrated compensation film 120. The polarizer 110 and the compensation film 120 are respectively the same as described above, and may prevent a display device from having visibility deterioration caused by light inflowing from the outside after passing the polarizer 110 and being reflected by a metal such as an electrode and the like in the organic light emitting panel 400. Accordingly, display characteristics of the organic light emitting device may be improved.

Hereinafter, a liquid crystal display (LCD) is described as an example of the display device.

Figure 5:
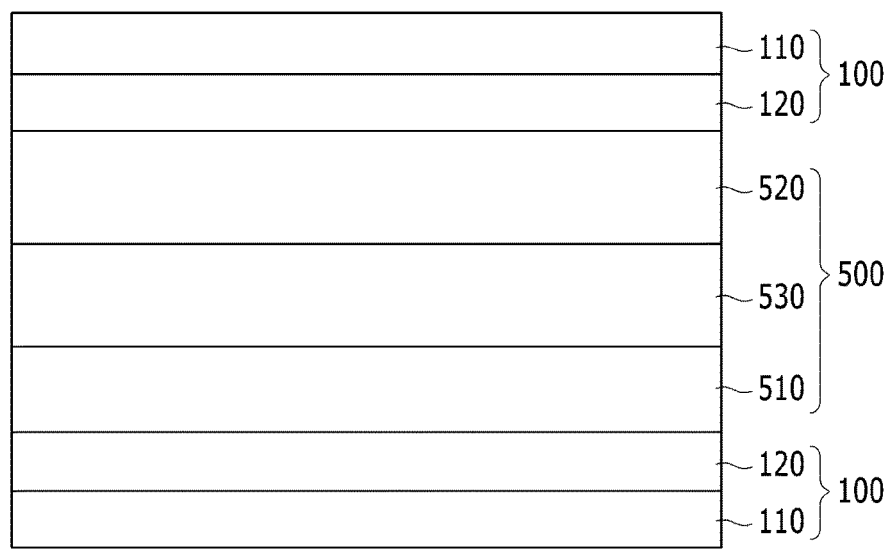
FIG. 5 is a schematic cross-sectional view showing a liquid crystal display according to an embodiment.

FIG. 5 is a schematic cross-sectional view showing a liquid crystal display according to an embodiment.

Referring to FIG. 5, the liquid crystal display (LCD) according to an embodiment includes a liquid crystal display panel 500, and an optical film 100 positioned on one side or both sides of the liquid crystal panel 500.

The liquid crystal panel 500 may be a twist nematic (TN) mode panel, a vertical alignment (PVA) mode panel, an in-plane switching (IPS) mode panel, an optically compensated bend (OCB) mode panel, or the like.

The liquid crystal panel 500 may include a first display panel 510, a second display panel 520, and a liquid crystal layer 530 interposed between the first display panel 510 and the second display panel 520.

The first display panel 510 may include, for example, a thin film transistor (not shown) formed on a substrate (not shown) and a first electric field generating electrode (not shown) connected to the same, and the second display panel 520 may include, for example, a color filter (not shown) formed on a substrate (not shown) and a second electric field generating electrode (not shown). However, it is not limited thereto, and the color filter may be included in the first display panel 510, while the first electric field generating electrode and the second electric field generating electrode may be disposed on the first display panel 510 together therewith.

The liquid crystal layer 530 may include a plurality of liquid crystal molecules. The liquid crystal molecules may have positive or negative dielectric anisotropy. When the liquid crystal molecules have positive dielectric anisotropy, the major axes thereof may be aligned substantially parallel to the surface of the first display panel 510 and the second display panel 520 when an electric field is not applied, and the major axes may be aligned substantially perpendicular to the surface of the first display panel 510 and second display panel 520 when an electric field is applied. On the other hand, when the liquid crystal molecules have negative dielectric anisotropy, the major axes may be aligned substantially perpendicular to the surface of the first display panel 510 and the second display panel 520 when an electric field is not applied, and the major axes may be aligned substantially parallel to the surface of the first display panel 510 and the second display panel 520 when an electric field is applied.

The optical film 100 may be disposed on the outside of the liquid crystal panel 500. Although the optical film 100 is shown to be provided on both the lower part and the upper part of the liquid crystal panel 500 in the drawing, it is not limited thereto, and it may be formed on only one of the lower part and the upper part of the liquid crystal panel 500.

Hereinafter, the present disclosure is illustrated in more detail with reference to examples. However, these examples are exemplary, and the present disclosure is not limited thereto.

EXAMPLES

Synthesis of Monomer

Synthesis Example 1

1) Step 1

Reaction Scheme 1

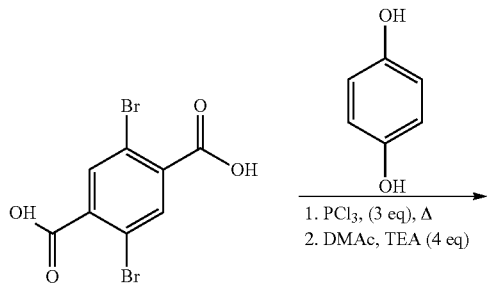

9.72 grams (g) of 2,5-dibromoterephthalic acid (MW=323.92 grams per mole (g/mol), 30 millimoles (mmol), 1.0 equivalents (eq)) is placed in 260 mL of toluene, and the mixture is stirred. Subsequently, 18.74 g of $PCl_5$ (MW=208.24 g/mol, 90 mmol, 3.0 eq) and one drop of pyridine are added thereto, and the obtained mixture is heated at 80 to 90° C. After the crystals are completely dissolved, the mixture is additionally stirred for one hour. Subsequently, the reaction solution is distilled, to obtaining a yellow oily compound. Then, 50 milliliters (mL) of N,N-dimethyl acetamide is added thereto, and the obtained mixture is uniformly stirred (a mixed solution A). In a separate vessel, hydroquinone (MW=110.11 g/mol, 300 mmol, 10.0 eq) is added to 50 mL of N,N-dimethyl acetamide and heated until the solid is completely dissolved. Then, 12.14 g of triethylamine (MW=101.19 g/mol, 120 mmol, 4.0 eq) is added to the solution and mixed (a mixed solution B). The mixed solution B is slowly added to the mixed solution A, and the mixture is stirred at room temperature for 1 hour. When the reaction is complete, the reaction solution is poured into 1,600 mL of purified water to form crystals. The crystallization solution is then heated for about 1 hour and filtered while heated, to obtain pink crystals. Additionally, 1,000 mL of water is added thereto, and the mixture is heated and stirred for about 1 hour. The resultant is filtered while heated, and crystals obtained therefrom are vacuum-dried in a drying oven (60° C.) for greater than or equal to 12 hours, to obtain 11.12 g of a gray compound I-1 (a yield of 73%). The compound I-1 is used in the following reaction without an additional purification.

$^1$H NMR (DMSO-$d_6$) 300 MHz, δ, ppm: 6.8 (d, 4H), 7.2 (d, 4H), 8.4 (s, 2H), 9.6 (s, 2H).

2) Step 2

Reaction Scheme 2

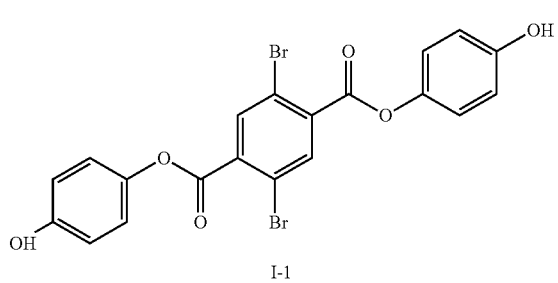

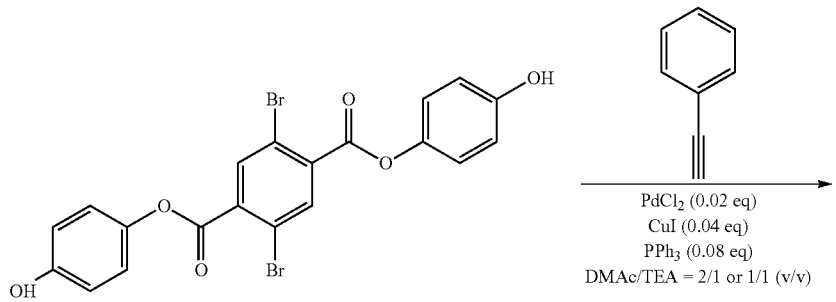

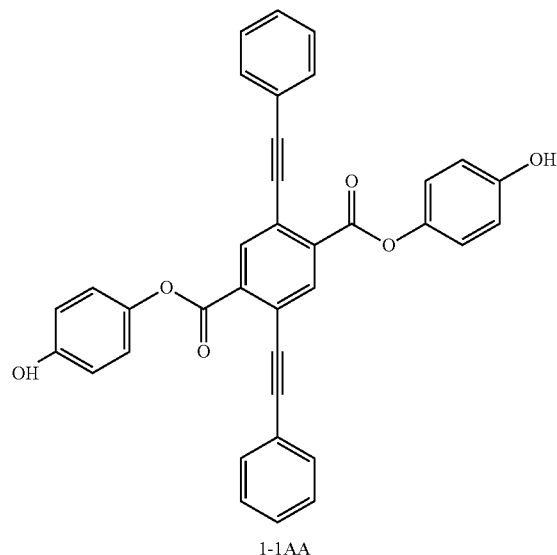

1-1AA 5.08 g of the compound I-1 (MW=508.118 g/mol, 10 mmol, 1.0 eq) and 140 mL of N,N-dimethyl acetamide are stirred under a nitrogen atmosphere and slowly heated for about 30 minutes. Subsequently, phenylacetylene (MW=102.14 g/mol, 30 mmol, 3.0 eq, m=3.006 g), palladium(II) chloride (PdCl$_2$) (MW=177.33 g/mol, 0.50 mmol, 0.05 eq, m=0.09 g), copper(I) iodide (CuI) (MW=190.45 g/mol, 1.89 mmol, 0.19 eq, m=0.36 g), triphenylphosphine (PPh$_3$, MW=262.45 g/mol, 3.62 mmol, 0.36 eq, m=5.25 g), and 70 mL of triethylamine are added thereto, and the mixture is heated at about 80 to 100° C. for 20 hours to carry out a reaction. When the reaction is complete, 1,500 mL of water is poured thereto to precipitate the crystals, and a weak hydrochloric acid solution is used to adjust its pH to 1-2. Subsequently, the crystals are filtered to obtain intensely brown crystals. Then, the brown crystals are placed in a mixed solution of 60 mL of water and 700 mL of methanol, and the crystals that were not dissolved are filtered and removed after heating the mixture for one hour. Then, the filtered crystallization solution is cooled to room temperature to collect the obtained crystals, 500 mL of chloroform is added to the collected crystals again, and the mixture is heated to dissolve the brown crystals. Subsequently, the solution is cooled to room temperature, to obtain 1.3 g of a yellow crystalline compound 1-1AA (a yield of 24%).

$^1$H NMR (DMSO-d$_6$) 300 MHz, δ, ppm: 6.8-6.9 (d, 4H), 7.1-7.2 (d, 4H), 7.4-7.6 (m, 10H), 8.4-8.5 (s, 2H), 9.5-9.6 (s, 2H).

Synthesis of Polymer and Preparation of Polymer Film

Synthesis Example 2

Reaction Scheme 3

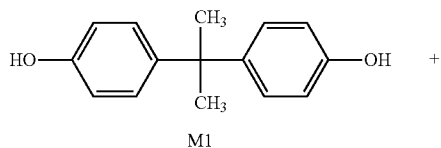

M1

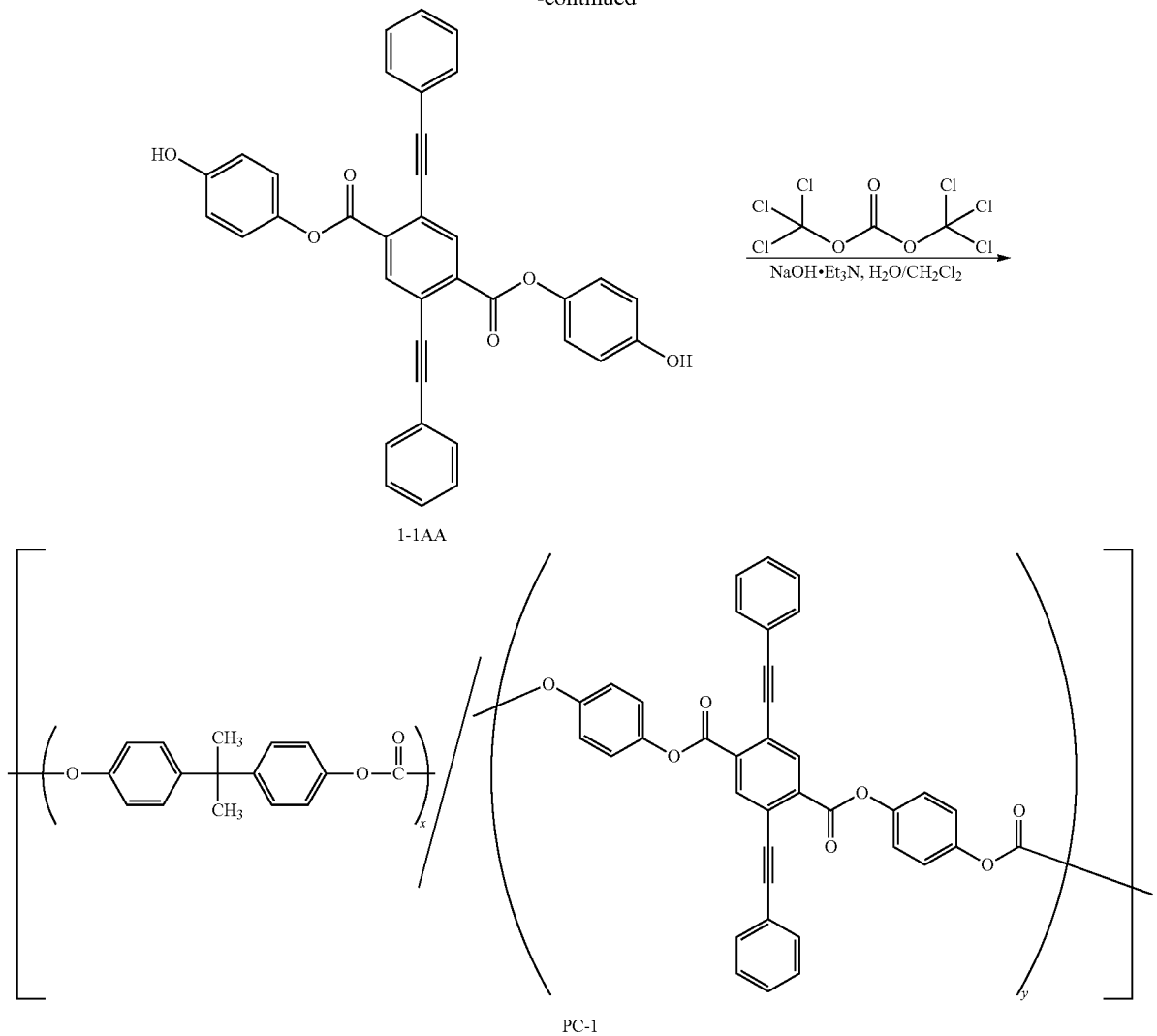

Sodium hydroxide (MW=40.0 g/mol, 5.69 mmol, 5.0 eq, m=1.14 g) is placed in a 200 mL flask equipped with a mechanical stirrer. 17 mL of water, 1.70 g of a compound M1, and 0.0395 g of the compound 1-1AA are placed therein. Herein, the compound M1 and the compound 1-1AA are supplied in a mole ratio of 99:1. Subsequently, 0.84 g of triphosgene dissolved in 17 mL of dichloromethane is added thereto, and the obtained mixture is stirred for 15 minutes. Then, 6 mg of triethylamine is added thereto, and the obtained mixture is stirred at room temperature for 90 minutes. Then, 17 mL of N,N-diacetamide is added thereto, and the mixture is stirred at room temperature for greater than or equal to 12 hours. When the reaction is complete, the resultant is diluted with dichloromethane, subsequently washed with 1%-hydrochloric acid and water, reprecipitated with methanol, and vacuum-dried at 60° C. for 12 hours, to obtain 1.68 g of a polymer PC-1 as a brown solid.

The polymer PC-1 is dissolved in a mixed solvent of tetrahydrofuran and dioxane (1/1, volume to volume (v/v)), to prepare a polymer solution having a concentration of 20 percent by weight (wt %). Subsequently, the polymer solution is coated on a glass substrate and dried at 40° C. for 1 hour and at 80° C. for 1 hour to form a polymer film. Then, the polymer film is stripped from the glass substrate to manufacture a 96 micrometer (μm)-thick polymer film.

Synthesis Example 3

An 83 μm-thick a polymer film is manufactured by forming a polymer PC-1 according to the same method as Synthesis Example 2 except for supplying 1.70 g of the compound M1 and 0.125 g of the compound 1-1AA (97:3 of a mole ratio).

Synthesis Example 4

A 97 μm-thick a polymer film is manufactured by forming a polymer PC-1 according to the same method as Synthesis Example 2 except for supplying 1.70 g of the compound M1 and 0.214 g of the compound 1-1AA (95:5 of a mole ratio).

Synthesis Example 5

A 63 μm-thick a polymer film is manufactured by forming a polymer PC-1 according to the same method as Synthesis Example 2 except for supplying 1.61 g of the compound M1 and 0.291 g of the compound 1-1AA (93:7 of a mole ratio).

Synthesis Example 6

A 32 μm-thick a polymer film is manufactured by forming a polymer PC-1 according to the same method as Synthesis Example 2 except for supplying 1.40 g of the compound M1 and 0.427 g of the compound 1-1AA (90:10 of a mole ratio).

Synthesis Example 7 ratio of 90:10. Subsequently, 0.84 g of triphosgene dissolved in 17 mL of dichloromethane is added thereto, and the mixture is stirred for 15 minutes. Then, 6 mg of triethylamine is added thereto, and the obtained mixture is stirred at room temperature for 90 minutes. Then, 17 mL of N,N-diacetamide is added thereto, and the obtained mixture is stirred at room temperature for greater than or equal to 12 hours. When the reaction is complete, the resultant is diluted with dichloromethane, washed with 1%-hydrochloric acid and water, reprecipitated with methanol, and vacuum-dried at 60° C. for 12 hours, to obtain 1.82 g of a polymer PC-2 as a brown solid.

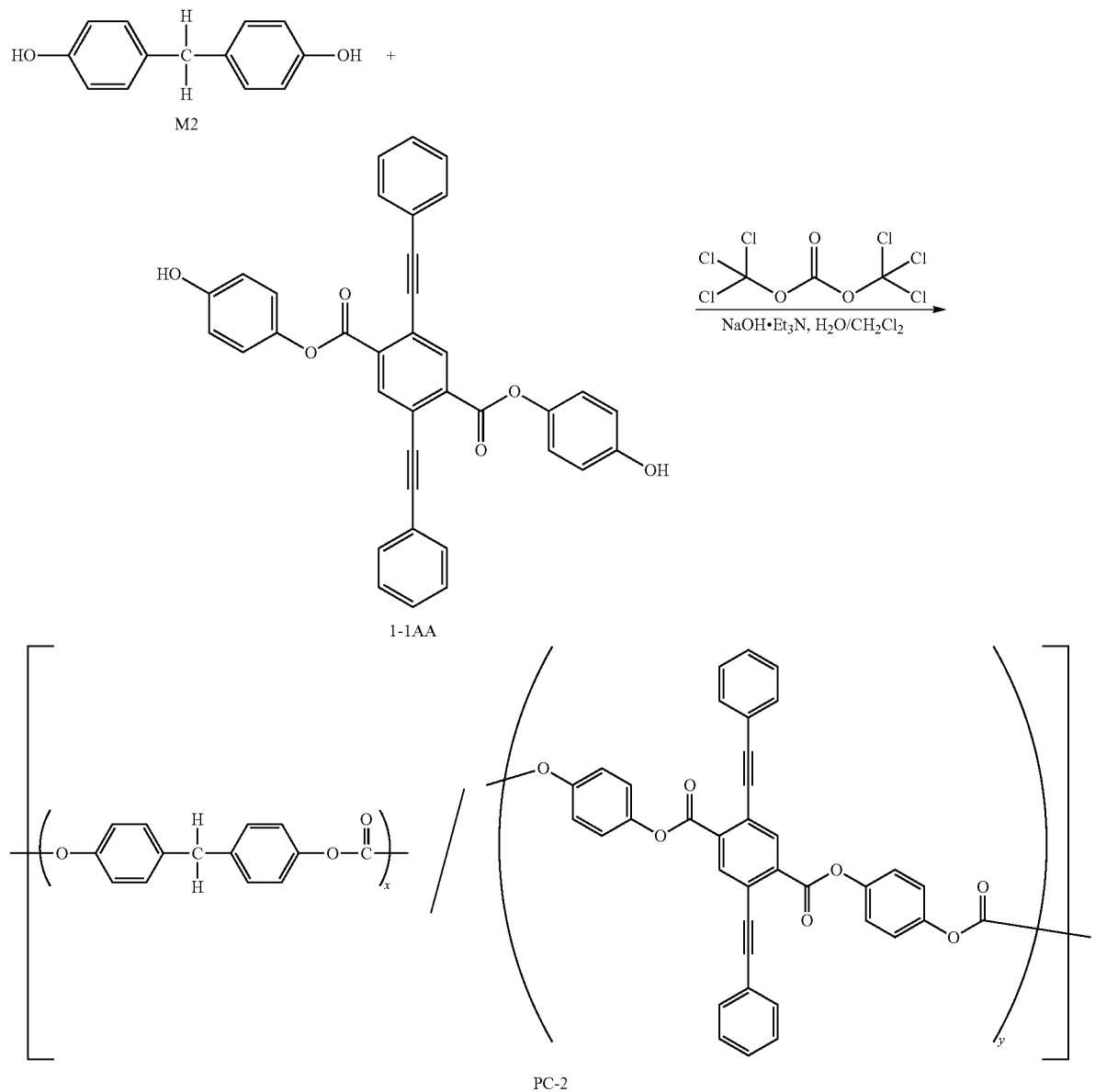

PC-2

1.14 g of sodium hydroxide (MW=40.0 g/mol, 5.69 mmol, 5.0 eq), 17 mL of water, 1.00 g of a compound M2, and 0.304 g of the compound 1-1AA are placed in a 200 mL flask equipped with a mechanical stirrer. Herein, the compound M2 and the compound 1-1AA are supplied in a mole The polymer PC-2 is dissolved in a mixed solvent of tetrahydrofuran and dioxane (1/1, v/v) to prepare a polymer solution having a concentration of 20 wt %. Subsequently, the polymer solution is coated on a glass substrate and dried at 40° C. for 1 hour and then, at 80° C. for 1 hour to form a polymer film. Then, the polymer film is stripped off the glass substrate to manufacture a 33 μm-thick polymer film.

Synthesis Example 8

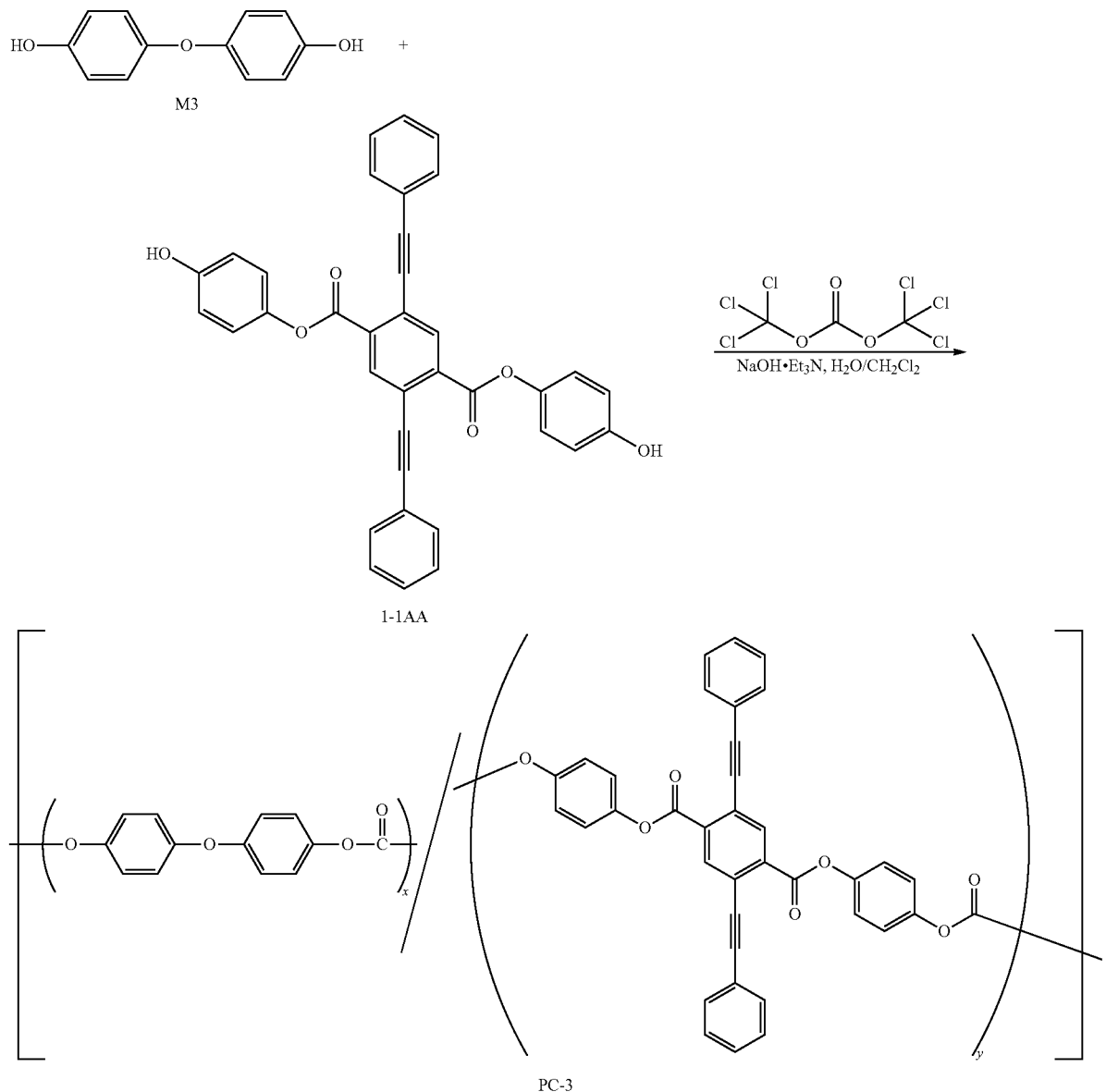

Sodium hydroxide (MW=40.0 g/mol, 5.69 mmol, 5.0 eq, 1.14 g) is placed in a 200 mL flask equipped with a mechanical stirrer. 17 mL of water, 1.20 g of a compound M3, and 0.363 g of the compound 1-1AA are placed therein. Herein, the compound M3 and the compound 1-1AA are supplied in a mole ratio of 90:10. Then, 0.84 g of triphosgene dissolved in 17 mL of dichloromethane is added thereto, and the obtained mixture is stirred for 15 minutes. Then, 6 mg of triethylamine is added thereto, and the obtained mixture is stirred at room temperature for 90 minutes. Then, 17 mL of N,N-diacetamide is added thereto, and the obtained mixture is stirred at room temperature for greater than or equal to 12 hours. When the reaction is complete, the resultant is diluted with dichloromethane, washed with 1%-hydrochloric acid and water, reprecipitated with methanol, and vacuum-dried at 60° C. for 12 hours to obtain 1.82 g of a polymer PC-3 as a brown solid.

The polymer PC-3 is dissolved in a mixed solvent of tetrahydrofuran and dioxane (1/1, v/v) to prepare a polymer solution having a concentration of 20 wt %. Subsequently, the polymer solution is coated on a glass substrate and dried at 40° C. for 1 hour and at 80° C. for 1 hour to form a polymer film. Then, the polymer film is detached from the glass substrate to manufacture a 33 μm-thick polymer film.

Synthesis Example 9

The polymer PC-1 according to Synthesis Example 6 and a polymer having a structural unit represented by Chemical Formula 5a in a mole ratio of 1:9 are dissolved in tetrahydrofuran and dioxane (1/1, v/v) to prepare a polymer solution having a concentration of 20 wt %. The polymer solution is coated on a glass substrate and dried at 40° C. for 1 hour and at 80° C. for 1 hour to manufacture a 74 μm-thick polymer film.

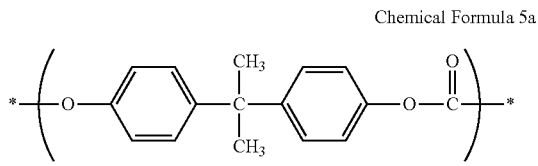

Chemical Formula 5a

Synthesis Example 10

An 83 μm-thick polymer film is manufactured according to the same method as Synthesis Example 9 except for mixing the polymer PC-1 according to Synthesis Example 6 and a polymer having a structural unit represented by Chemical Formula 5a in a mole ratio of 2:8.

Synthesis Example 11

An 80 μm-thick polymer film is manufactured according to the same method as Synthesis Example 9 except for mixing the polymer PC-1 according to Synthesis Example 6 and a polymer having a structural unit represented by Chemical Formula 5a in a mole ratio of 3:7.

Evaluation 1

Light transmittance of the polymer films according to Synthesis Examples 2 to 11 is evaluated.

The light transmittance is measured by using a KONICA MINOLTA Spectrophotometer CM-3600.

The results are provided in Table 1.

TABLE 1

| | Light transmittance (%) |
|---|---|
| Synthesis Example 2 | 85.2 |
| Synthesis Example 3 | 86.2 |
| Synthesis Example 4 | 78.1 |
| Synthesis Example 5 | 67.6 |
| Synthesis Example 6 | 84.4 |
| Synthesis Example 7 | 84.1 |
| Synthesis Example 8 | 85.1 |
| Synthesis Example 9 | 84.2 |
| Synthesis Example 10 | 83.0 |
| Synthesis Example 11 | 77.5 |

The polymer films according to Synthesis Examples 2 to 11 have satisfactory light transmittance of greater than or equal to about 60%.

Preparation of Compensation Film

Example 1

The polymer film according to Synthesis Example 2 is cut into a size of 1×1 square centimeters ($cm^2$) to prepare a sample, and a 54 μm-thick elongation compensation film is manufactured by fixing the long side of the sample on a metal frame, heating the sample to 145° C. in an oven for one hour under a nitrogen atmosphere and 3.6 times elongating it at 10 degrees Centigrade per minute (° C./min).

Example 2

An about 44 μm-thick elongation compensation film is manufactured by cutting the polymer film according to Synthesis Example 3 into a size of 1×1 $cm^2$ to prepare a sample, fixing one long end of the sample on a metal frame, heating the sample to 145° C. at 10° C./min for 1 hour in an oven under a nitrogen atmosphere, and 4.0 times elongating it.

Example 3

An about 51 μm-thick elongation compensation film is manufactured by cutting the polymer film according to Synthesis Example 4 into a size of 1×1 $cm^2$ to prepare a sample, fixing one long end of the sample on a metal frame, heating the sample to 145° C. at 10° C./min for 1 hour in an oven under a nitrogen atmosphere, and 3.4 times elongating it.

Example 4

An about 57 μm-thick elongation compensation film is manufactured by cutting the polymer film according to Synthesis Example 9 into a size of 1×1 $cm^2$ to prepare a sample, fixing one long end of the sample on a metal frame, heating the sample to 145° C. at 10° C./min for 1 hour in an oven under a nitrogen atmosphere, and 3.2 times elongating it.

Example 5

An about 58 μm-thick elongation compensation film is manufactured by cutting the polymer film according to Synthesis Example 10 into a size of 1×1 $cm^2$ to prepare a sample, fixing one long end of the sample on a metal frame, heating the sample to 145° C. at 10° C./min for 1 hour in an oven under a nitrogen atmosphere and 3.2 times elongating it.

Example 6

An about 68 μm-thick elongation compensation film is manufactured by cutting the polymer film according to Synthesis Example 11 into a size of 1×1 $cm^2$ to prepare a sample, fixing one long end of the sample on a metal frame, heating the sample to 145° C. at 10° C./min for 1 hour in an oven under a nitrogen atmosphere, and 1.8 times elongating it.

Evaluation 2

In-phase retardation values, thickness direction retardation values, and wavelength dispersion of the compensation film according to Examples 1 to 6 are evaluated.

The in-phase retardation values and thickness direction retardation values are measured using an Axoscan equipment (Axometrics, Inc.).

Wavelength dispersion of in-phase retardation values and in-phase retardation values are shown in Table 2.

TABLE 2

| | $R_o$ (550 nm) | $R_o$ (450 nm)/ $R_o$ (550 nm) | $R_o$ (650 nm)/ $R_o$ (550 nm) |
|---|---|---|---|
| Example 1 | 134 | 1.07 | 0.96 |
| Example 2 | 680 | 1.01 | 0.98 |
| Example 3 | 347 | 1.03 | 0.96 |
| Example 4 | 122 | 1.07 | 0.98 |
| Example 5 | 98.3 | 1.09 | 0.96 |
| Example 6 | 38.7 | 1.13 | 0.95 |

Wavelength dispersion of thickness direction retardation values and thickness direction retardation values are shown in Table 3.

TABLE 3

| | $R_{th}$ (550 nm) | $R_{th}$ (450 nm)/ $R_{th}$ (550 nm) | $R_{th}$ (650 nm)/ $R_{th}$ (550 nm) |
|---|---|---|---|
| Example 1 | 63.4 | 1.03 | 1.00 |
| Example 2 | 282 | 0.98 | 1.02 |
| Example 3 | 162 | 1.06 | 0.99 |
| Example 4 | 71.2 | 1.02 | 0.97 |
| Example 5 | 65.3 | 0.98 | 1.04 |
| Example 6 | 14.7 | 1.13 | 0.95 |

Referring to Tables 2 and 3, the compensation films according to Examples 1 to 6 have a forward wavelength dispersion phase delay where a retardation of light at a shorter wavelength is larger than a retardation of light at a longer wavelength, or a reverse wavelength dispersion phase delay where a retardation of light at a longer wavelength is larger than a retardation of light at a shorter wavelength. From the results, it is understood that compensation films having desirable retardation values and wavelength dispersion may be realized by controlling various factors such as a nature and content ratios of a polymer, and elongation rates of films.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A monomer represented by Chemical Formula 1:

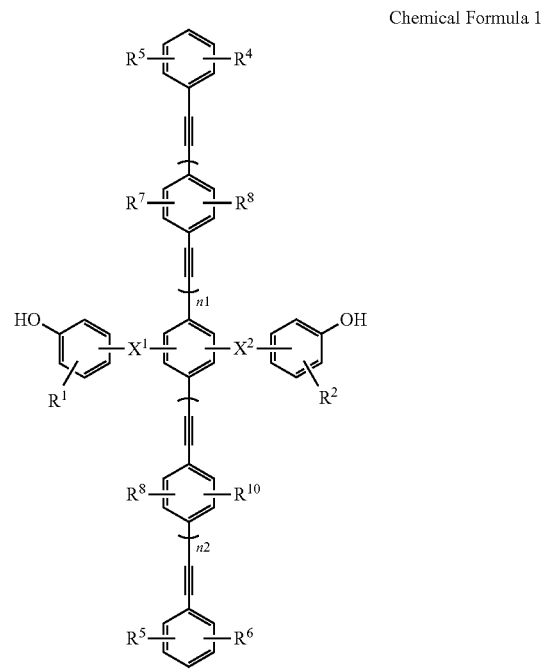

Chemical Formula 1 wherein in Chemical Formula 1, $X^1$ and $X^2$ are independently O, C(=O), or C(=O)O, $R^1$ to $R^{10}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and n1 and n2 are independently an integer ranging from 0 to 3.

2. The monomer of claim 1, wherein the monomer is represented by Chemical Formula 1-1 or 1-2:

Chemical Formula 1-1

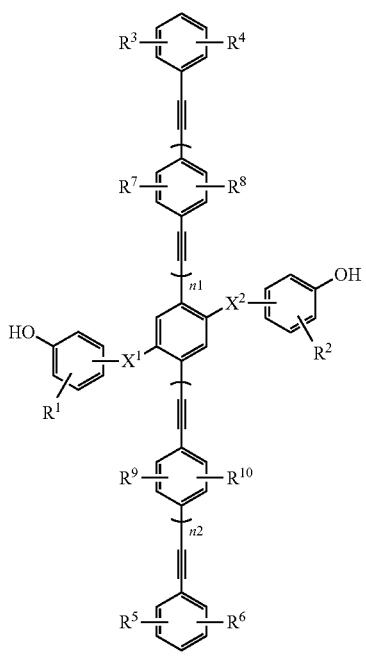

Chemical Formula 1-2

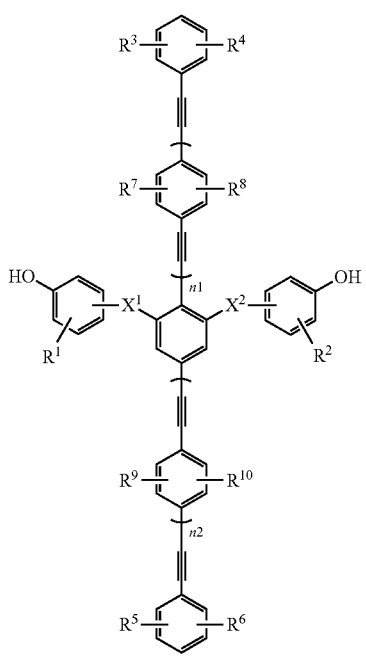

wherein in Chemical Formula 1-1 and 1-2, $X^1$ and $X^2$ are independently O, C(=O), or C(=O)O, $R^1$ to $R^{10}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and n1 and n2 are independently an integer ranging from 0 to 3.

3. The monomer of claim 1, wherein the monomer is represented by one of Chemical Formula 1-1A to 1-2D:

Chemical Formula 1-1A

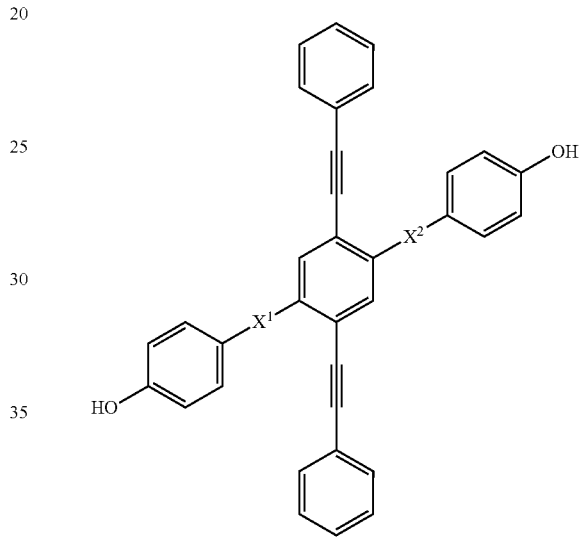

Chemical Formula 1-1B

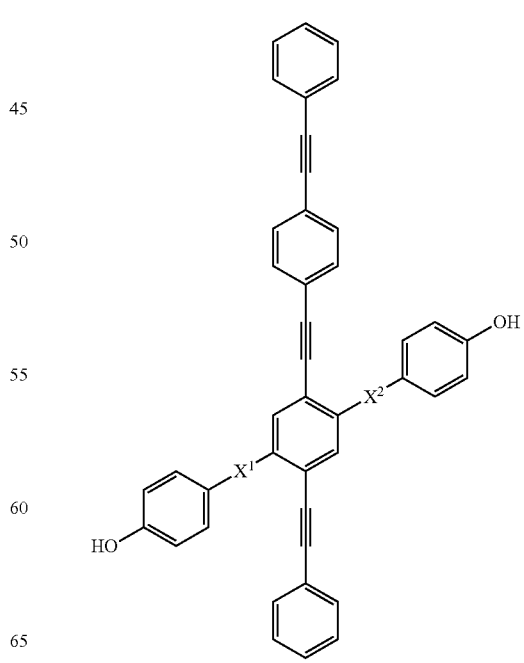

Chemical Formula 1-1C
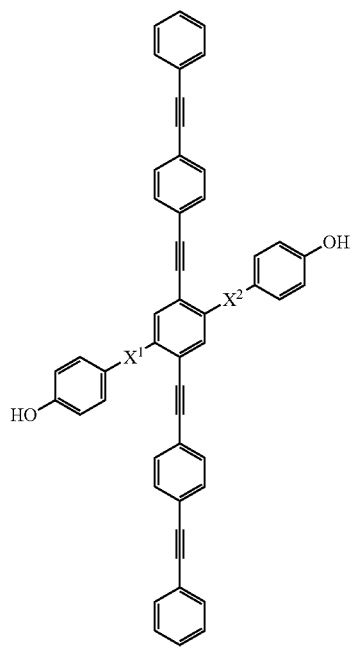
Chemical Formula 1-2B
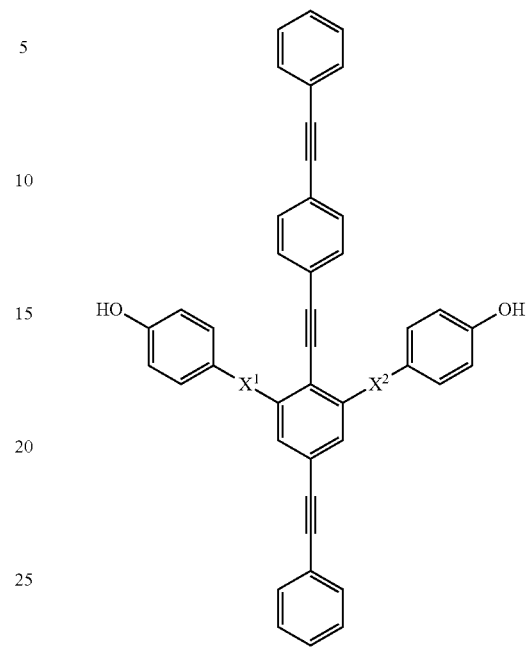
Chemical Formula 1-2A
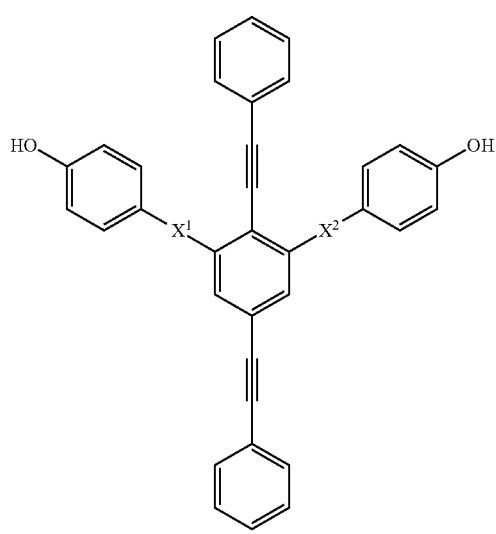
Chemical Formula 1-2C
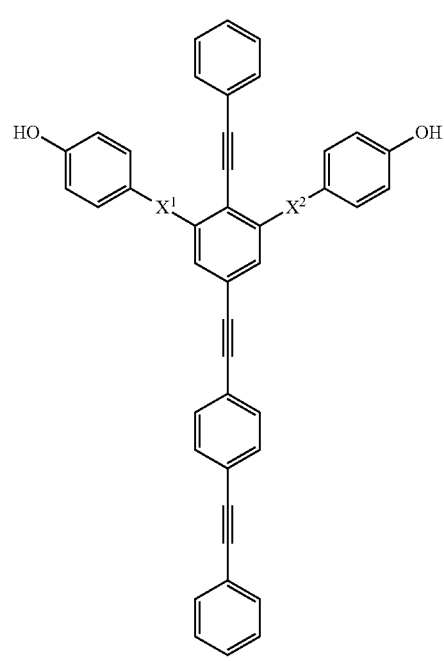

Chemical Formula 1-2D

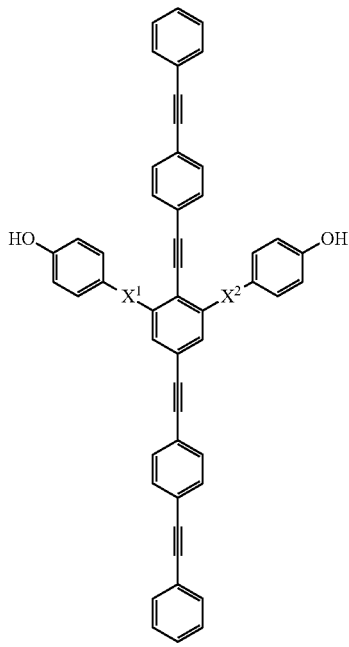

wherein in Chemical Formula 1-1A to 1-2D,
$X^1$ and $X^2$ are independently O, C(=O), or C(=O)O.

4. A polymer comprising a structural unit derived from the monomer of claim 1.

5. The polymer of claim 4, wherein the structural unit is derived from a reaction product of the monomer with a carbonate or a derivative thereof.

6. A polymer comprising a first structural unit represented by Chemical Formula 3:

Chemical Formula 3

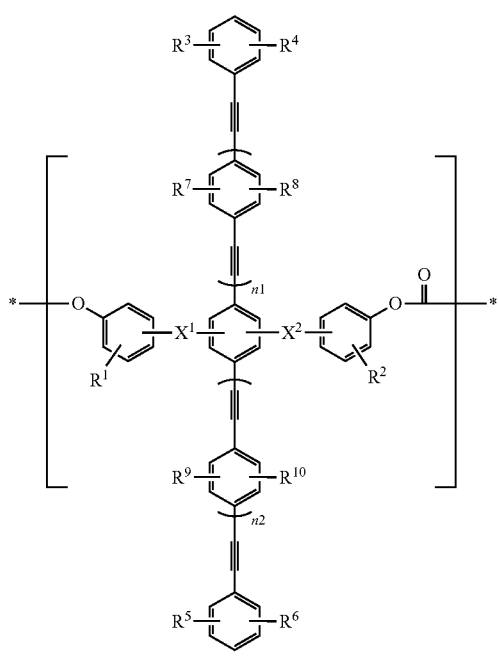

wherein in Chemical Formula 3, $X^1$ and $X^2$ are independently O, C(=O), or C(=O)O, $R^1$ to $R^{10}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and n1 and n2 are independently an integer ranging from 0 to 3.

7. The polymer of claim 6, wherein the first structural unit is represented by Chemical Formula 3-1 or 3-2:

Chemical Formula 3-1

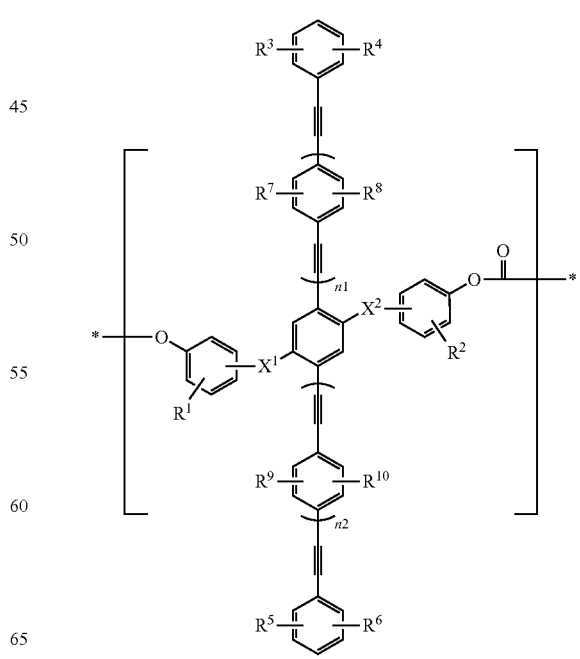

Chemical Formula 3-2

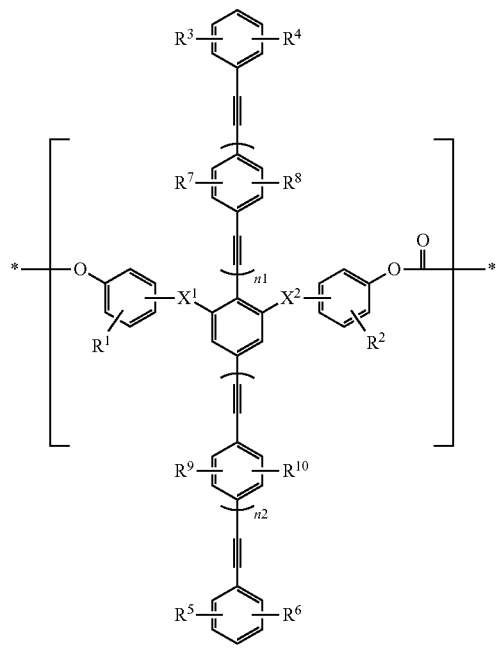

wherein in Chemical Formula 3-1 and 3-2, $X^1$ and $X^2$ are independently O, C(=O), or C(=O)O, $R^1$ to $R^{10}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and n1 and n2 are independently an integer ranging from 0 to 3.

8. The polymer of claim 6, wherein the first structural unit is represented by one of Chemical Formula 3-1A to 3-2D:

Chemical Formula 3-1A

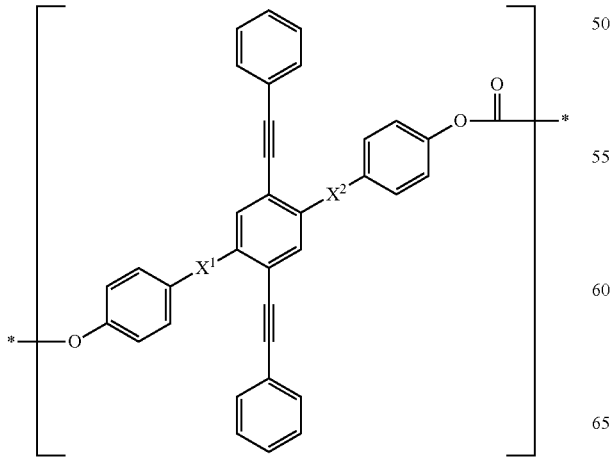

Chemical Formula 3-1B

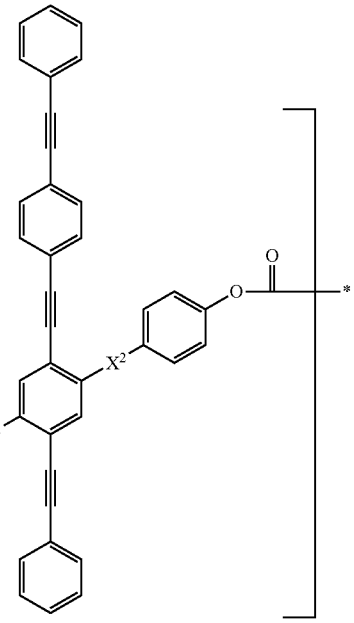

Chemical Formula 3-1C

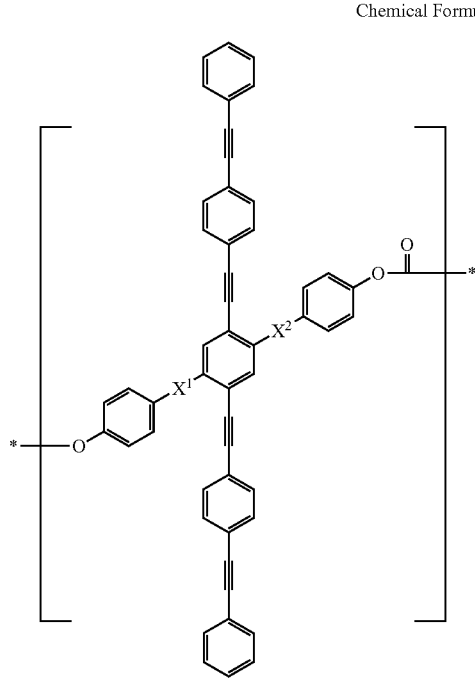

-continued
Chemical Formula 3-2A
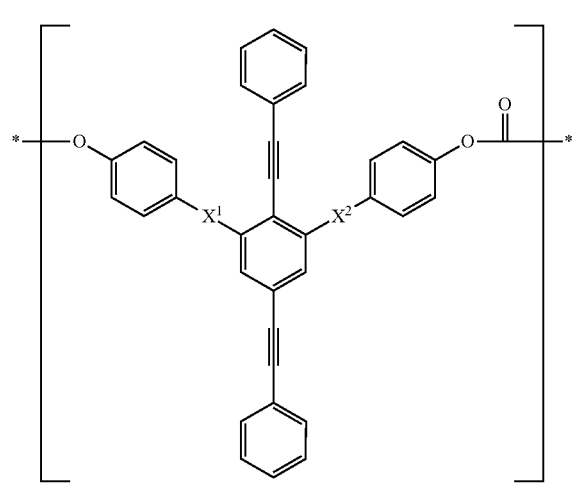
Chemical Formula 3-2B
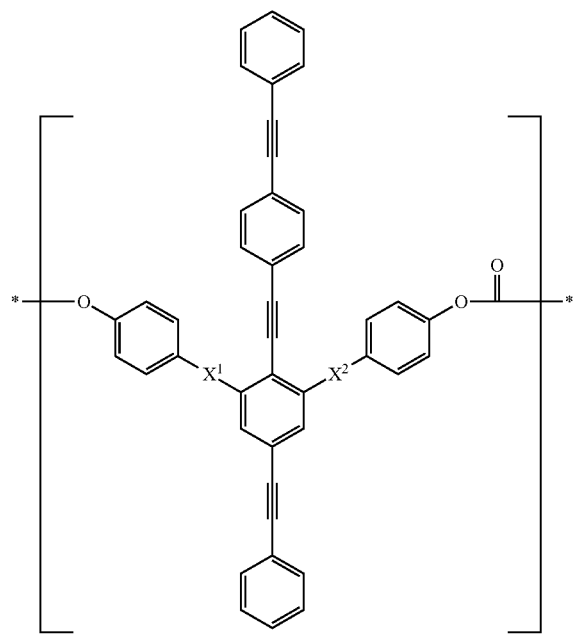
Chemical Formula 3-2C
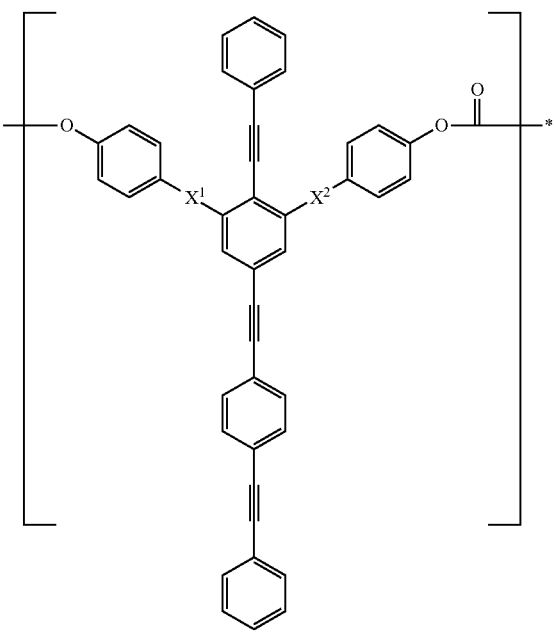
Chemical Formula 3-2D
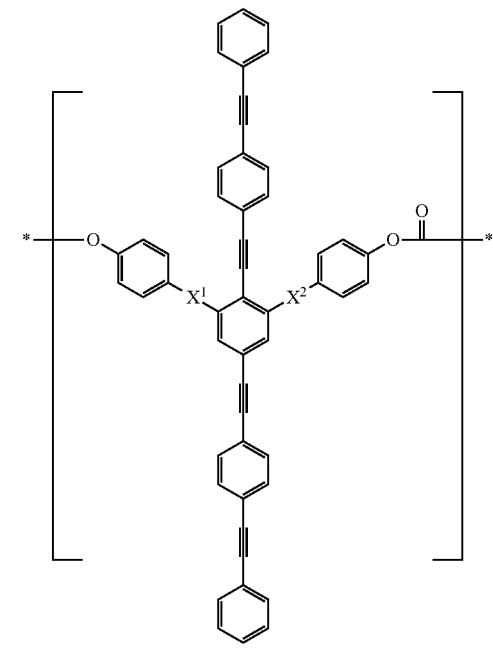

wherein in Chemical Formula 3-1A to 3-2D,

X¹ and X² are independently O, C(=O), or C(=O)O.

9. The polymer of claim 6, wherein the polymer further comprises a second structural unit represented by Chemical Formula 4:

Chemical Formula 4

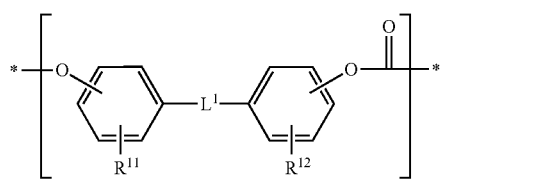

wherein in Chemical Formula 4,

L¹ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, O, C(=O), C(=O)O, SO₂, or a combination thereof, and R¹¹ and R¹² are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof.

10. The polymer of claim 9, wherein a mole ratio of the first structural unit and the second structural unit is about 0.1:99.9 to about 10.0:90.0.

11. The polymer of claim 9, wherein a mole ratio of the first structural unit and the second structural unit is about 1:99 to about 5:95.

12. A compensation film comprising a polymer comprising a structural unit derived from the monomer of claim 1.

13. The compensation film of claim 12, wherein the structural unit is derived from a reaction product of the monomer with a carbonate or a derivative thereof.

14. The compensation film of claim 12, wherein the compensation film is elongated in a uniaxial or biaxial direction.

15. A compensation film comprising a first polymer comprising a first structural unit represented by Chemical Formula 3:

Chemical Formula 3 wherein in Chemical Formula 3,

X¹ and X² are independently O, C(=O), or C(=O)O,

R¹ to R¹⁰ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and n1 and n2 are independently an integer ranging from 0 to 3.

16. The compensation film of claim 15, wherein the first structural unit is represented by Chemical Formula 3-1 or 3-2:

Chemical Formula 3-1

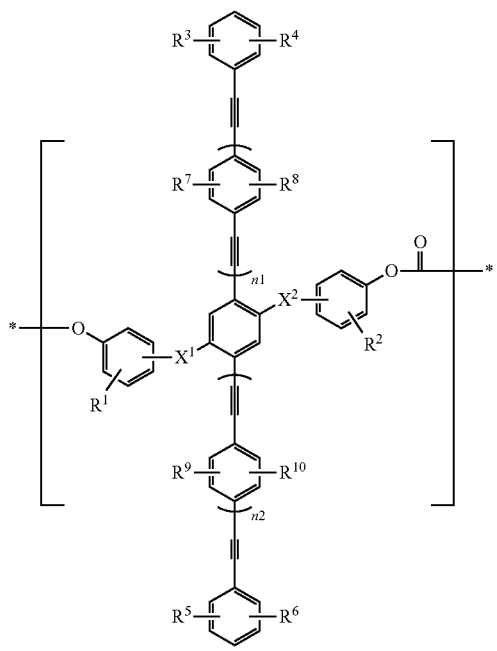

Chemical Formula 3-2

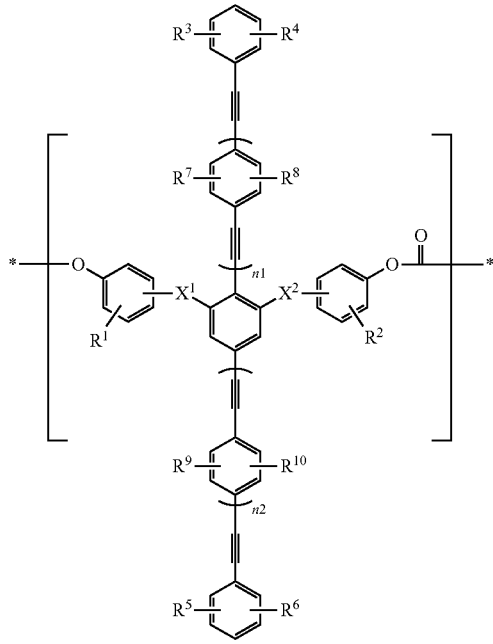

wherein in Chemical Formula 3-1 and 3-2, $X^1$ and $X^2$ are independently O, C(=O), or C(=O)O, $R^1$ to $R^{10}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof, and n1 and n2 are independently an integer ranging from 0 to 3.

17. The compensation film of claim 15, wherein the first structural unit is represented by one of Chemical Formula 3-1A to 3-2D:

Chemical Formula 3-1A

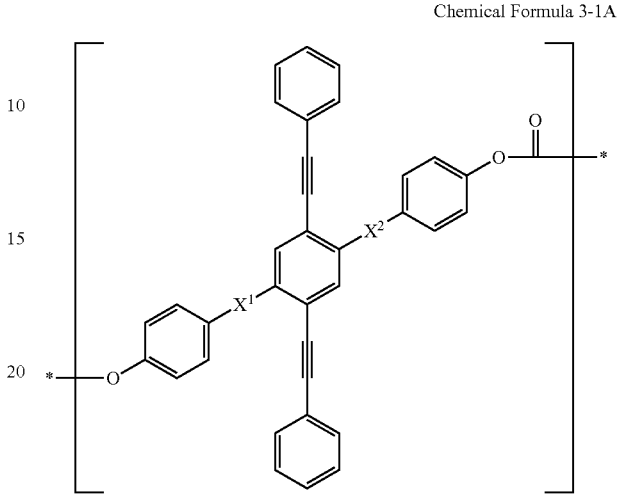

Chemical Formula 3-1B

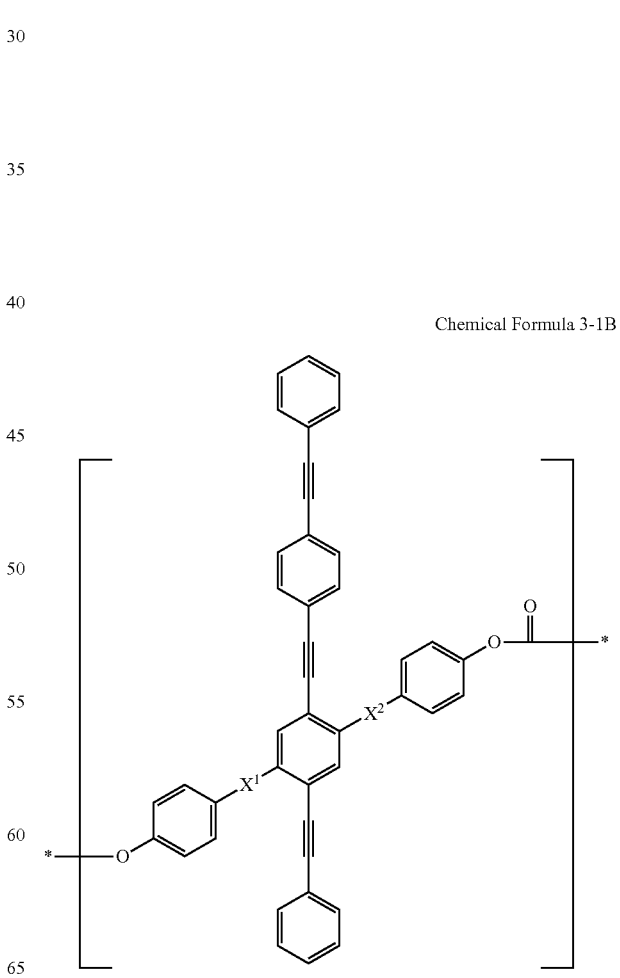

Chemical Formula 3-1C
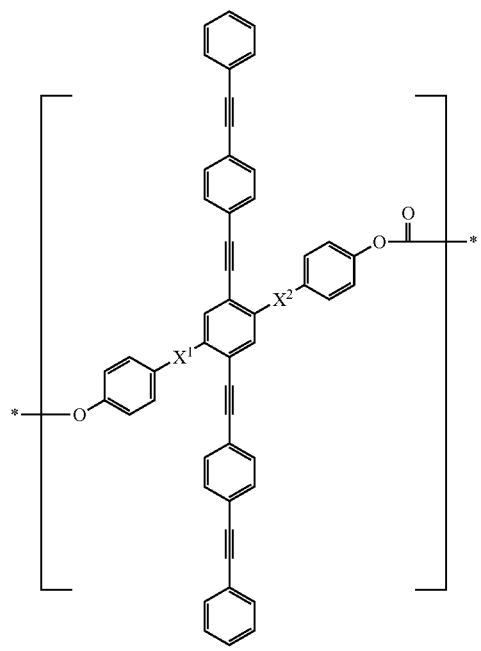
Chemical Formula 3-2B
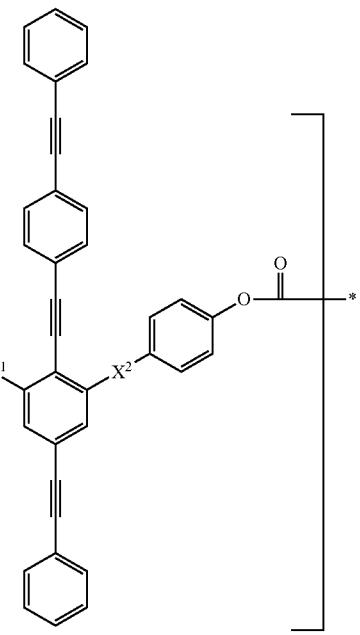
Chemical Formula 3-2A
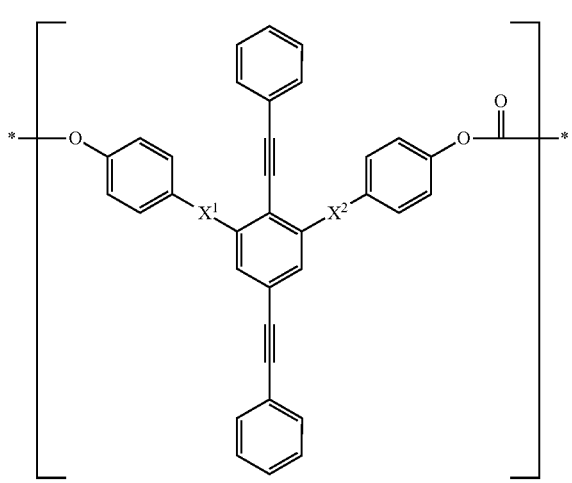
Chemical Formula 3-2C
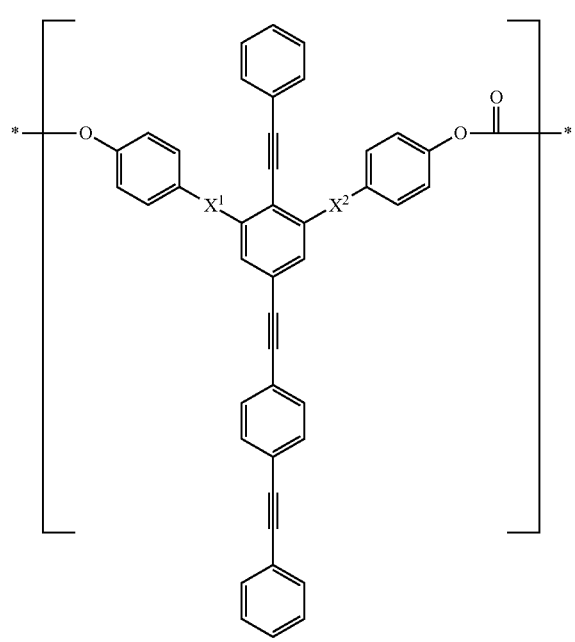

-continued

Chemical Formula 3-2D

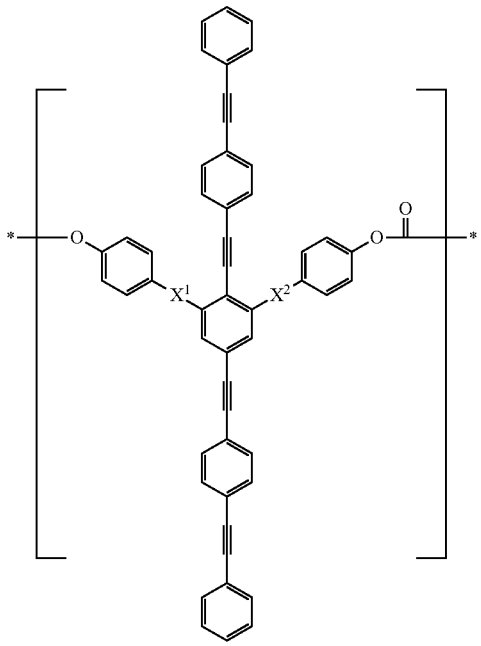

wherein in Chemical Formula 3-1A to 3-2D,
$X^1$ and $X^2$ are independently O, C(=O), or C(=O)O.

18. The compensation film of claim 15, wherein the first polymer further comprises a second structural unit represented by Chemical Formula 4:

Chemical Formula 4

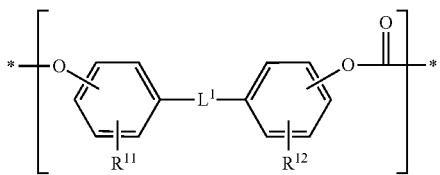

wherein in Chemical Formula 4,
$L^1$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, O, C(=O), C(=O)O, SO$_2$, or a combination thereof, and
$R^{11}$ and $R^{12}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof.

19. The compensation film of claim 18, wherein the first polymer comprises the first structural unit and the second structural unit in a mole ratio of about 0.1:99.9 to about 10.0:90.0.

20. The compensation film of claim 18, wherein the first polymer comprises the first structural unit and the second structural unit in a mole ratio of about 1:99 to about 5:95.

21. The compensation film of claim 18, further comprising a second polymer comprising a structural unit represented by Chemical Formula 5:

Chemical Formula 5

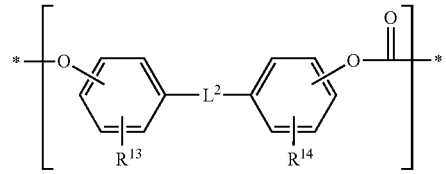

wherein in Chemical Formula 5,
$L^2$ is a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C3 to C20 divalent heterocyclic group, O, C(=O), C(=O)O, SO$_2$, or a combination thereof, and
$R^{13}$ and $R^{14}$ are independently hydrogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C20 aryl group, a substituted or unsubstituted C3 to C20 heterocyclic group, a substituted or unsubstituted silyl group, a hydroxy group, a halogen, a nitro group, or a combination thereof.

22. The compensation film of claim 21, comprising the first polymer and the second polymer in a mole ratio of about 1:9 to about 3:7.

23. The compensation film of claim 15, wherein the compensation film is elongated in a uniaxial or biaxial direction.

24. The compensation film of claim 15, wherein retardation values at 450 nanometer wavelength, 550 nanometer wavelength, and 650 nanometer wavelength of the compensation film satisfy one of Relationship Equations 1 to 5:

| | |
|---|---|
| $R(450\ nm) \geq R(550\ nm) > R(650\ nm)$ | Relationship Equation 1 |
| $R(450\ nm) > R(550\ nm) \geq R(650\ nm)$ | Relationship Equation 2 |
| $R(450\ nm) = R(550\ nm) = R(650\ nm)$ | Relationship Equation 3 |
| $R(450\ nm) \leq R(550\ nm) < R(650\ nm)$ | Relationship Equation 4 |
| $R(450\ nm) < R(550\ nm) \leq R(650\ nm)$ | Relationship Equation 5 | wherein in Relationship Equations 1 to 5,
$R(450\ nm)$ is in-plane retardation or thickness direction retardation at a 450 nanometer wavelength,
$R(550\ nm)$ is in-plane retardation or thickness direction retardation at a 550 nanometer wavelength, and
$R(650\ nm)$ is in-plane retardation or thickness direction retardation at a 650 nanometer wavelength.

25. An optical film comprising:
the compensation film of claim 15, and
a polarizer.

26. A display device comprising the compensation film of claim 15.

27. A display device comprising the optical film of claim 25.

* * * * *